(12) United States Patent
Cadet et al.

(10) Patent No.: US 7,285,655 B2
(45) Date of Patent: Oct. 23, 2007

(54) NUCLEIC ACIDS ENCODING OPIATE RECEPTORS

(75) Inventors: Patrick Cadet, Elmont, NY (US); George B. Stefano, Melville, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/454,213

(22) Filed: Jun. 15, 2006

(65) Prior Publication Data

US 2006/0229444 A1    Oct. 12, 2006

Related U.S. Application Data

(63) Continuation of application No. 10/080,917, filed on Feb. 22, 2002, now Pat. No. 7,094,892.

(60) Provisional application No. 60/336,677, filed on Dec. 5, 2001, provisional application No. 60/270,479, filed on Feb. 22, 2001.

(51) Int. Cl.
C07H 21/04 (2006.01)

(52) U.S. Cl. .................................. 536/23.5

(58) Field of Classification Search ..................... None
See application file for complete search history.

(56) References Cited

U.S. PATENT DOCUMENTS

| | | | |
|---|---|---|---|
| 4,683,195 A | 7/1987 | Mullis et al. | |
| 4,873,191 A | 10/1989 | Wagner et al. | |
| 5,580,859 A | 12/1996 | Felgner et al. | |
| 5,589,466 A | 12/1996 | Felgner et al. | |

FOREIGN PATENT DOCUMENTS

| | | |
|---|---|---|
| WO | WO95/01548 | 1/1995 |
| WO | WO99/24471 | 5/1999 |
| WO | WO 00/04046 | 1/2000 |

OTHER PUBLICATIONS

Birren B. et al. Database GenEmbl. Accession No. AC027439, Jun. 14, 2000.*
GenBank Accession No. AC027439 dated Jun. 14, 2000, 55 pages.
Cadet et al., "Molecular Identification and Functional Expression of μ3, a Novel Alternatively Spliced Variant of the Human μ Opiate Receptor Gene," *J. Immunol.*, 2003, 170:5118-5123.
Fimiani et al., "μ3 Opiate receptor expression in lung and lung carcinoma: ligand binding and coupling to nitric oxide release," *Cancer Letters*, 1999, 146:45-51.
Gossler et al., "Transgenesis by means of blastocyst-derived embryonic stem cell lines," *Proc. Natl. Acad. Sci. USA*, 1986, 83:9065-9069.
Lo, "Transformation by Iontophoretic Microinjection of DNA: Multiple Integrations Without Tandem Insertions," *Mol. Cell. Biol.*, 1983, 3(10):1803-1814.
Magazine et al., "Morphine-Induced Conformational Changes in Human Monocytes, Granulocytes, and Endothelial Cells and in Invertebrate Immunocytes and Microglia Are Mediated by Nitric Oxide," *J. Immunol.*, 1996, 156:4845-4850.
Mestek et al., "The Human μ Opioid Receptor: Modulation of Functional Desensitization by Calcium/Calmodulin-Dependent Protein Kinase and Protein Kinase C," *J. Neurosci.*, 1995, 15(3):2396-2406.
Sambrook et al., *Molecular Cloning—A Laboratory Manual*, 1989, Second Edition, Cold Spring Harbor Laboratory Press, Plainview, NY, Sections 7.39-7.52.
Schnicke et al., "Human Factor IX Transgenic Sheep Produced by Transfer of Nuclei from Transfected Fetal Fibroblasts," *Science*, 1997, 278:2130-2133.
Stefano et al., "Opiate-like substances in an invertebrate, an opiate receptor on invertebrate and human immunocytes, and a role in immunosuppression," *Proc. Natl. Acad. Sci. USA*, 1993, 90:11099-11103.
Stefano et al., "Presence of the μ3 Opiate Receptor in Endothelial Cells," *J. Biol. Chem.*, 1995, 270(51):30290-30293.
Stefano, "The Mu3 Opiate Subtype," *Pain Forum*, 1999, 8(4):206-209.
Thompson et al., "Germ Line Transmission and Expression of a Corrected HPRT Gene Produced by Gene Targeting in Embryonic Stem Cells," *Cell*, 1989, 56:313-321.
Van der Putten et al., "Efficient insertion of genes into the mouse germ line viaretroviral vectors," *Proc. Natl. Acad. Sci. USA*, 1985, 82:6148-6152.
Wang et al., "Human mu opiate receptor. CDNA and genomic clones, pharmacologic characterization and chromosomal assignment," Sequence Comparison B, *FEBS Lett.*, 1994, 388(2):217-222.
Zimprich et al., "Cloning and expression of an isoform of the rat μ opiod receptor (rMOR1B) which differs in agonist induced desensitization from rMOR1," *FEBS Letters*, 1995, 359:142-146.

* cited by examiner

*Primary Examiner*—Robert S. Landsman
(74) *Attorney, Agent, or Firm*—Fish & Richardson P.C.

(57) ABSTRACT

The invention provides isolated nucleic acid molecules, host cells that contain an isolated nucleic acid molecule, and substantially pure polypeptides. For example, the invention provides isolated nucleic acid molecules that encode polypeptides having mu3 opiate receptor activity, host cells that contain an isolated nucleic acid molecule that encodes a polypeptide having mu3 opiate receptor activity, and substantially pure polypeptides that have mu3 opiate receptor activity. In addition, the invention provides methods and materials for identifying mu3 opiate receptor agonists and antagonists.

13 Claims, 4 Drawing Sheets

NUCLEIC ACIDS ENCODING OPIATE RECEPTORS

CROSS-RELATED APPLICATIONS

This application is a continuation of U.S. application Ser. No. 10/080,917, filed Feb. 22, 2002 now U.S. Pat. No. 7,094,892, which claims the benefit of U.S. Provisional Application Ser. No. 60/270,479, filed Feb. 22, 2001 and U.S. Provisional Application Ser. No. 60/336,677, filed Dec. 5, 2001.

STATEMENT AS TO FEDERALLY SPONSORED RESEARCH

Funding for the work described herein was provided by the federal government under NIDA number 5R24DA09010. Thus, the federal government may have certain rights in the invention.

BACKGROUND

1. Technical Field

The invention relates to opiate receptors. Specifically, the invention relates to mu3 and mu4 opiate receptors as well as mu3 and mu4 opiate receptor activation and inhibition.

2. Background Information

Three general classes of cell surface opioid receptors (kappa, delta, and mu) have been described based on ligand specificity. Opioid receptors exhibiting high binding specificity for morphine have been designated mu opioid receptors. Detailed analysis of mu opioid receptors from various tissues has revealed the existence of multiple mu opioid receptor subtypes. In fact, the cDNA encoding the mu1 opioid receptor subtype has been identified. Oligonucleotides complementary to some, but not all, exons of the mu1 opioid receptor can block the effects mediated by the mu1 and mu2 receptor subtypes. Thus, the mu1 and mu2 opioid receptor subtypes appear to share exon sequences, as would be expected of splice variants. Supporting the idea of alternative splicing is the finding of a single mu gene in human and mouse chromosomal DNA. In addition, a novel rat brain mu opioid receptor subtype, designated rMOR1B, has been identified. This receptor is identical to the rat mu1 opioid receptor at its N-terminus but differs in its length and sequence at the C-terminus. Further, affinity studies demonstrated that the substrate specificity of rMOR1B is similar to that of the rat mu1 opioid receptor, but rMOR1B is more resistant to agonist-induced desensitization and has a different expression pattern in brain. The presence of another opiate receptor, designated mu3 opiate receptor, has been demonstrated pharmacologically. This mu3 opiate receptor is opioid peptide insensitive and opiate alkaloid selective. In addition, detailed binding analysis indicates that the mu3 opiate receptor is expressed by immune tissues (e.g., human monocytes and granulocytes).

SUMMARY

The invention relates to opiate receptors such as mu3 and mu4 opiate receptors. Specifically, the invention provides isolated nucleic acid molecules that encode polypeptides having mu3 opiate receptor activity, host cells that contain an isolated nucleic acid molecule that encodes a polypeptide having mu3 opiate receptor activity, and substantially pure polypeptides that have mu3 opiate receptor activity. In addition, the invention provides methods and materials for identifying mu3 opiate receptor agonists and antagonists.

The present invention is based on the discovery of nucleic acid that encodes a polypeptide having mu3 opiate receptor activity. The term "mu3 opiate receptor" as used herein refers to a cell surface polypeptide that has a higher affinity for morphine than that for the opioid polypeptide [Tyr-D-Ala$^2$, Gly-N-Me-Phe$^4$, Gly(ol)$^5$]-enkephalin (DAMGO; SEQ ID NO:29). The interaction of morphine with a mu3 opiate receptor can induce changes in intracellular calcium concentration and nitric oxide release. Isolated nucleic acid molecules that encode a polypeptide having mu3 opiate receptor activity, host cells containing such isolated nucleic acid molecules, and substantially pure polypeptides having mu3 opiate receptor activity are particularly useful to research scientists since these materials allow scientists to explore, for example, the interactions of morphine with the mu3 opiate receptor, the molecular mechanisms by which morphine induces intracellular calcium concentration changes, and the relationships of mu3 opiate receptors with other mu opioid receptors. In addition, the methods and materials described herein can be used to provide cells that are responsive to morphine. For example, cells can be transfected with a vector that directs expression of a polypeptide having mu3 opiate receptor activity such that those cells can respond to morphine stimulation.

In general, the invention features an isolated nucleic acid molecule that encodes a polypeptide having mu3 opiate receptor activity. The isolated nucleic acid molecule can contain a nucleic acid sequence with a length and a percent identity to the sequence set forth in SEQ ID NO:1 over the length, where the point defined by the length and the percent identity is within the area defined by points A, B, C, and D of FIG. 1, where point A has coordinates (81, 100), point B has coordinates (81, 65), point C has coordinates (15, 65), and point D has coordinates (15, 100). The polypeptide can contain an amino acid sequence with a length and a percent identity to the sequence set forth in SEQ ID NO:2 over the length, where the point defined by the length and the percent identity is within the area defined by points A, B, C, and D of FIG. 1, where point A has coordinates (26, 100), point B has coordinates (26, 65), point C has coordinates (5, 65), and point D has coordinates (5, 100). The isolated nucleic acid molecule can hybridizes under hybridization conditions to the sense or antisense strand of the sequence set forth in SEQ ID NO:1 or 3. The isolated nucleic acid molecule can contain the sequence set forth in SEQ ID NO:4, 6, 8, or 10.

In another embodiment, the invention features an isolated nucleic acid molecule that hybridizes under hybridization conditions to the sense or antisense strand of a nucleic acid that encodes a polypeptide having mu3 opiate receptor activity, where the isolated nucleic acid molecule is at least 12 nucleotides in length, and where the isolated nucleic acid molecule does not hybridize to the sense or antisense strand of the sequence set forth in SEQ ID NO:12 or 13.

Another embodiment of the invention features an isolated nucleic acid molecule containing a nucleic acid sequence with a length and a percent identity to the sequence set forth in SEQ ID NO:1 over the length, where the point defined by the length and the percent identity is within the area defined by points A, B, C, and D of FIG. 1, where point A has coordinates (81, 100), point B has coordinates (81, 65), point C has coordinates (15, 65), and point D has coordinates (15, 100). The isolated nucleic acid molecule can encode a polypeptide having mu3 opiate receptor activity.

In another aspect, the invention features a cell containing an isolated nucleic acid molecule that encodes a polypeptide having mu3 opiate receptor activity. The isolated nucleic acid molecule can contain a nucleic acid sequence with a length and a percent identity to the sequence set forth in SEQ ID NO:1 over the length, where the point defined by the length and the percent identity is within the area defined by points A, B, C, and D of FIG. 1, where point A has coordinates (81, 100), point B has coordinates (81, 65), point C has coordinates (15, 65), and point D has coordinates (15, 100). The polypeptide can contain an amino acid sequence with a length and a percent identity to the sequence set forth in SEQ ID NO:2 over the length, where the point defined by the length and the percent identity is within the area defined by points A, B, C, and D of FIG. 1, where point A has coordinates (26, 100), point B has coordinates (26, 65), point C has coordinates (5, 65), and point D has coordinates (5, 100). The isolated nucleic acid molecule can hybridize under hybridization conditions to the sense or antisense strand of the sequence set forth in SEQ ID NO:1 or 3. The isolated nucleic acid molecule can contain the sequence set forth in SEQ ID NO:4, 6, 8, or 10.

In another embodiment, the invention features a cell containing an isolated nucleic acid molecule that hybridizes under hybridization conditions to the sense or antisense strand of a nucleic acid that encodes a polypeptide having mu3 opiate receptor activity, where the isolated nucleic acid molecule is at least 12 nucleotides in length, and where the isolated nucleic acid molecule does not hybridize to the sense or antisense strand of the sequence set forth in SEQ ID NO:12 or 13.

Another aspect of the invention features a substantially pure polypeptide having mu3 opiate receptor activity. The polypeptide can be encoded by a nucleic acid sequence having a length and a percent identity to the sequence set forth in SEQ ID NO:1 over the length, where the point defined by the length and the percent identity is within the area defined by points A, B, C, and D of FIG. 1, where point A has coordinates (81, 100), point B has coordinates (81, 65), point C has coordinates (15, 65), and point D has coordinates (15, 100). The polypeptide can contain an amino acid sequence with a length and a percent identity to the sequence set forth in SEQ ID NO:2 over the length, where the point defined by the length and the percent identity is within the area defined by points A, B, C, and D of FIG. 1, where point A has coordinates (26, 100), point B has coordinates (26, 65), point C has coordinates (5, 65), and point D has coordinates (5, 100). The polypeptide can be encoded by a nucleic acid molecule that hybridizes under hybridization conditions to the sense or antisense strand of the sequence set forth in SEQ ID NO:1 or 3. The polypeptide can contain the sequence set forth in SEQ ID NO:5, 7, 9, or 11.

Another aspect of the invention features a method for identifying a mu3 opiate receptor agonist. The method includes (a) contacting a cell with a test molecule, where the cell contains an isolated nucleic acid molecule (e.g., exogenous nucleic acid molecule) that encodes a polypeptide having mu3 opiate receptor activity, and where the cell expresses the polypeptide, and (b) determining whether or not the test molecule induces, in the cell, a mu3 opiate receptor-mediated response. The determining step can include monitoring nitric oxide synthase activity in the cell. The monitoring nitric oxide synthase activity can include detecting nitric oxide release from the cell. A nitric oxide-specific amperometric probe can be used to detect the nitric oxide release. The determining step can include monitoring intracellular calcium levels within the cell. A fluorescent ion indicator can be used to monitor the intracellular calcium levels. The fluorescent ion indicator can be Fura-2. The determining step can contain monitoring nitric oxide synthase activity and intracellular calcium levels in the cell.

Another aspect of the invention features a method for identifying a mu3 opiate receptor antagonist. The method includes (a) contacting a cell with a test molecule and a mu3 opiate receptor agonist, where the cell contains an isolated nucleic acid molecule (e.g., exogenous nucleic acid molecule) that encodes a polypeptide having mu3 opiate receptor activity, and where the cell expresses the polypeptide, and (b) determining whether or not the test molecule reduces or prevents, in the cell, a mu3 opiate receptor-mediated response induced by the mu3 opiate receptor agonist. The mu3 opiate receptor agonist can contain morphine or dihydromorphine. The determining step can include monitoring nitric oxide synthase activity in the cell. The determining step can include monitoring intracellular calcium levels within the cell.

Another aspect of the invention features an isolated nucleic acid molecule containing a nucleic acid sequence with a length and a percent identity to the sequence set forth in SEQ ID NO:22 over the length, where the point defined by the length and the percent identity is within the area defined by points A, B, C, and D of FIG. 1, where point A has coordinates (225, 100), point B has coordinates (225, 65), point C has coordinates (15, 65), and point D has coordinates (15, 100).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
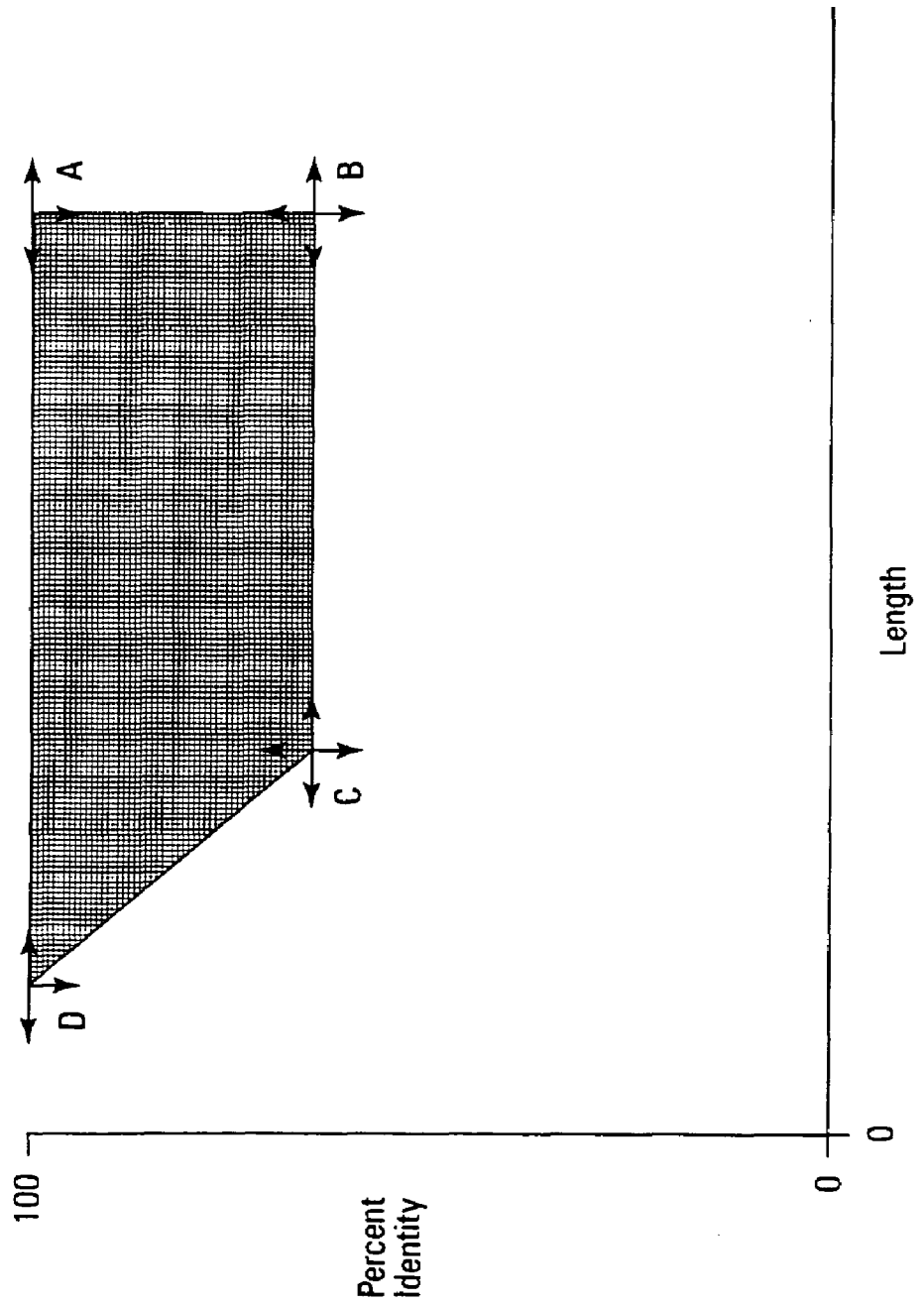
FIG. 1 is a graph plotting length and percent identity with points A, B, C, and D defining an area indicated by shading.

The invention provides isolated nucleic acid molecules, host cells that contain an isolated nucleic acid molecule, and substantially pure polypeptides. In addition, the invention provides methods and materials for identifying mu3 opiate receptor agonists and antagonists.

Nucleic Acids

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, all non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally-occurring can be exogenous to a particular cell. For example, an entire chromosome isolated from a cell of person X is an exogenous nucleic acid with respect to a cell of person Y once that chromosome is introduced into Y's cell.

The invention provides isolated nucleic acid molecules that contain a nucleic acid sequence having (1) a length, and (2) a percent identity to an identified nucleic acid sequence over that length. The invention also provides isolated nucleic acid molecules that contain a nucleic acid sequence encoding a polypeptide that contains an amino acid sequence having (1) a length, and (2) a percent identity to an identified amino acid sequence over that length. Typically, the identified nucleic acid or amino acid sequence is a sequence referenced by a particular sequence identification number, and the nucleic acid or amino acid sequence being compared to the identified sequence is referred to as the target sequence. For example, an identified sequence can be the sequence set forth in SEQ ID NO:1.

A length and percent identity over that length for any nucleic acid or amino acid sequence is determined as follows. First, a nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the State University of New York—Old Westbury campus library as well as at Fish & Richardson's web site ("www" dot "fr" dot "com") or the U.S. government's National Center for Biotechnology Information web site ("www" dot "ncbi" dot "nlm" dot "nih" dot "gov"). Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq1.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. For example, the following command can be used to generate an output file containing a comparison between two sequences: C:\Bl2seq −i c:\seq1.txt −j c:\seq2.txt −p blastn −o c:\output.txt −q −1 −r 2. To compare two amino acid sequences, the options of Bl2seq are set as follows: −i is set to a file containing the first amino acid sequence to be compared (e.g., C:\seq1.txt); −j is set to a file containing the second amino acid sequence to be compared (e.g., C:\seq2.txt); −p is set to blastp; −o is set to any desired file name (e.g., C:\output.txt); and all other options are left at their default setting. For example, the following command can be used to generate an output file containing a comparison between two amino acid sequences: C:\Bl2seq –i c:\seq1.txt –j c:\seq2.txt –p blastp –o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive nucleotides or amino acid residues from the target sequence presented in alignment with sequence from the identified sequence starting with any matched position and ending with any other matched position. A matched position is any position where an identical nucleotide or amino acid residue is presented in both the target and identified sequence. Gaps presented in the target sequence are not counted since gaps are not nucleotides or amino acid residues. Likewise, gaps presented in the identified sequence are not counted since target sequence nucleotides or amino acid residues are counted, not nucleotides or amino acid residues from the identified sequence.

The percent identity over a determined length is determined by counting the number of matched positions over that length and dividing that number by the length followed by multiplying the resulting value by 100. For example, if (1) a 1000 nucleotide target sequence is compared to the sequence set forth in SEQ ID NO:4, (2) the Bl2seq program presents 200 nucleotides from the target sequence aligned with a region of the sequence set forth in SEQ ID NO:4 where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., 180÷200*100=90).

It will be appreciated that a single nucleic acid or amino acid target sequence that aligns with an identified sequence can have many different lengths with each length having its own percent identity. For example, a target sequence containing a 20 nucleotide region that aligns with an identified sequence as follows has many different lengths including those listed in Table 1.

```
                        1                   20
Target Sequence:        AGGTCGTGTACTGTCAGTCA
                        | || ||| ||| ||| |
Identified Sequence:    ACGTGGTGAACTGCCAGTGA
```

TABLE I

| Starting Position | Ending Position | Length | Matched Positions | Percent Identity |
|---|---|---|---|---|
| 1 | 20 | 20 | 15 | 75.0 |
| 1 | 18 | 18 | 14 | 77.8 |
| 1 | 15 | 15 | 11 | 73.3 |
| 6 | 20 | 15 | 12 | 80.0 |
| 6 | 17 | 12 | 10 | 83.3 |
| 6 | 15 | 10 | 8 | 80.0 |
| 8 | 20 | 13 | 10 | 76.9 |
| 8 | 16 | 9 | 7 | 77.8 |

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The invention provides isolated nucleic acid molecules containing a nucleic acid sequence that has at least one length and percent identity over that length as determined above such that the point defined by that length and percent identity is within the area defined by points A, B, C, and D of FIG. 1. In addition, the invention provides isolated nucleic acid molecules containing a nucleic acid sequence that encodes a polypeptide containing an amino acid sequence that has at least one length and percent identity over that length as determined above such that the point defined by that length and percent identity is within the area defined by points A, B, C, and D of FIG. 1. The point defined by a length and percent identity over that length is that point on the X/Y coordinate of FIG. 1 where the X axis is the length and the Y axis is the percent identity. Thus, the point defined by a nucleic acid sequence with a length of 200 and a percent identity of 90 has coordinates (200, 90). For the purpose of this invention, any point that falls on point A, B, C, or D is considered within the area defined by points A, B, C, and D of FIG. 1. Likewise, any point that falls on a line that defines the area defined by points A, B, C, and D is considered within the area defined by points A, B, C, and D of FIG. 1.

It will be appreciated that the term "the area defined by points A, B, C, and D of FIG. 1" as used herein refers to that area defined by the lines that connect point A with point B, point B with point C, point C with point D, and point D with point A. Points A, B, C, and D can define an area having any shape defined by four points (e.g., square, rectangle, or rhombus). In addition, two or more points can have the same coordinates. For example, points B and C can have identical coordinates. In this case, the area defined by points A, B, C, and D of FIG. 1 is triangular. If three points have identical coordinates, then the area defined by points A, B, C, and D of FIG. 1 is a line. In this case, any point that falls on that line would be considered within the area defined by points A, B, C, and D of FIG. 1. If all four points have identical coordinates, then the area defined by points A, B, C, and D of FIG. 1 is a point. In all cases, simple algebraic equations can be used to determine whether a point is within the area defined by points A, B, C, and D of FIG. 1.

It is noted that FIG. 1 is a graphical representation presenting possible positions of points A, B, C, and D. The shaded area illustrated in FIG. 1 represents one possible example, while the arrows indicate that other positions for points A, B, C, and D are possible. In fact, points A, B, C, and D can have any X coordinate and any Y coordinate. For example, point A can have an X coordinate equal to the number of nucleotides or amino acid residues in an identified sequence, and a Y coordinate of 100. Point B can have an X coordinate equal to the number of nucleotides or amino acid residues in an identified sequence, and a Y coordinate less than or equal to 100 (e.g., 50, 55, 65, 70, 75, 80, 85, 90, 95, and 99). Point C can have an X coordinate equal to a percent (e.g., 1, 2, 5, 10, 15, or more percent) of the number of nucleotides or amino acid residues in an identified sequence, and a Y coordinate less than or equal to 100 (e.g., 50, 55, 65, 70, 75, 80, 85, 90, 95, and 99). Point D can have an X coordinate equal to the length of a typical PCR primer (e.g., 12, 13, 14, 15, 16, 17, or more) or antigenic polypeptide (e.g., 5, 6, 7, 8, 9, 10, 11, 12, or more), and a Y coordinate less than or equal to 100 (e.g., 50, 55, 65, 70, 75, 80, 85, 90, 95, and 99).

Isolated nucleic acid molecules containing a nucleic acid sequence having a length and a percent identity to the sequence set forth in SEQ ID NO:1 over that length are within the scope of the invention provided the point defined by that length and percent identity is within the area defined by points A, B, C, and D of FIG. 1; where point A has an X coordinate less than or equal to 81, and a Y coordinate less than or equal to 100; where point B has an X coordinate less than or equal to 81, and a Y coordinate greater than or equal to 65; where point C has an X coordinate greater than or equal to 15, and a Y coordinate greater than or equal to 65; and where point D has an X coordinate greater than or equal to 15, and a Y coordinate less than or equal to 100. For example, the X coordinate for point A can be 81, 75, 70, 65, 50, or less; and the Y coordinate for point A can be 100, 99, 95, 90, 85, 80, 75, or less. The X coordinate for point B can be 81, 75, 70, 65, 50, or less; and the Y coordinate for point B can be 65, 70, 75, 80, 85, 90, 95, 99 or more. The X coordinate for point C can be 15, 16, 17, 18, 19, 20, 25, 30, 40, 50, 75, or more; and the Y coordinate for point C can be 65, 70, 75, 80, 85, 90, 95, 99 or more. The X coordinate for point D can be 15, 16, 17, 18, 19, 20, 25, 30, 40, 50, 75, or more; and the Y coordinate for point D can be 100, 99, 95, 90, 85, 80, 75, or less. In one embodiment, point A can be (81, 100), point B can be (81, 95), point C can be (45, 95), and point D can be (45, 100).

Isolated nucleic acid molecules containing a nucleic acid sequence having a length and a percent identity to the sequence set forth in SEQ ID NO:3 over that length are within the scope of the invention provided the point defined by that length and percent identity is within the area defined by points A, B, C, and D of FIG. 1; where point A has an X coordinate less than or equal to 262, and a Y coordinate less than or equal to 100; where point B has an X coordinate less than or equal to 262, and a Y coordinate greater than or equal to 65; where point C has an X coordinate greater than or equal to 45, and a Y coordinate greater than or equal to 65; and where point D has an X coordinate greater than or equal to 12, and a Y coordinate less than or equal to 100. For example, the X coordinate for point A can be 262, 260, 255, 250, 245, or less; and the Y coordinate for point A can be 100, 99, 95, 90, 85, 80, 75, or less. The X coordinate for point B can be 262, 260, 255, 250, 245, or less; and the Y coordinate for point B can be 65, 70, 75, 80, 85, 90, 95, 99 or more. The X coordinate for point C can be 45, 50, 60, 70, 80, 90, 100, 150, 200, or more; and the Y coordinate for point C can be 65, 70, 75, 80, 85, 90, 95, 99 or more. The X coordinate for point D can be 12, 13, 14, 15, 16, 17, 18, 19, 20, 25, 30, 40, 50, 75, 100, or more; and the Y coordinate for point D can be 100, 99, 95, 90, 85, 80, 75, or less. In one embodiment, point A can be (262, 100), point B can be (262, 95), point C can be (100, 95), and point D can be (100, 100).

Isolated nucleic acid molecules containing a nucleic acid sequence having a length and a percent identity to the sequence set forth in SEQ ID NO:22 over that length are within the scope of the invention provided the point defined by that length and percent identity is within the area defined by points A, B, C, and D of FIG. 1; where point A has an X coordinate less than or equal to 225, and a Y coordinate less than or equal to 100; where point B has an X coordinate less than or equal to 225, and a Y coordinate greater than or equal to 65; where point C has an X coordinate greater than or equal to 45, and a Y coordinate greater than or equal to 65; and where point D has an X coordinate greater than or equal to 12, and a Y coordinate less than or equal to 100. For example, the X coordinate for point A can be 225, 220, 215, 210, 205, 200, 175, 150, or less; and the Y coordinate for point A can be 100, 99, 95, 90, 85, 80, 75, or less. The X coordinate for point B can be 225, 220, 215, 210, 205, 200, 175, 150, or less; and the Y coordinate for point B can be 65, 70, 75, 80, 85, 90, 95, 99 or more. The X coordinate for point C can be 45, 50, 60, 70, 80, 90, 100, 150, 200, or more; and the Y coordinate for point C can be 65, 70, 75, 80, 85, 90, 95, 99 or more. The X coordinate for point D can be 12, 13, 14, 15, 16, 17, 18, 19, 20, 25, 30, 40, 50, 75, 100, or more; and the Y coordinate for point D can be 100, 99, 95, 90, 85, 80, 75, or less. In one embodiment, point A can be (225, 100), point B can be (225, 95), point C can be (100, 95), and point D can be (100, 100).

Isolated nucleic acid molecules containing a nucleic acid sequence that encodes a polypeptide containing an amino acid sequence having a length and a percent identity to the sequence set forth in SEQ ID NO:2 over that length are within the scope of the invention provided the point defined by that length and percent identity is within the area defined by points A, B, C, and D of FIG. 1; where point A has an X coordinate less than or equal to 26, and a Y coordinate less than or equal to 100; where point B has an X coordinate less than or equal to 26, and a Y coordinate greater than or equal to 50; where point C has an X coordinate greater than or equal to 10, and a Y coordinate greater than or equal to 50; and where point D has an X coordinate greater than or equal to 5, and a Y coordinate less than or equal to 100. For example, the X coordinate for point A can be 26, 25, 24, 23, 22, 21, 20, or less; and the Y coordinate for point A can be 100, 99, 95, 90, 85, 80, 75, or less. The X coordinate for point B can be 26, 25, 24, 23, 22, 21, 20, or less; and the Y coordinate for point B can be 50, 55, 60, 65, 70, 75, 80, 85, 90, 95, 99 or more. The X coordinate for point C can be 10, 12, 14, 16, 17, 18, 20, or more; and the Y coordinate for point C can be 50, 55, 60, 65, 70, 75, 80, 85, 90, 95, 99 or more. The X coordinate for point D can be 5, 6, 7, 8, 9, 10, 15, 20, or more; and the Y coordinate for point D can be 100, 99, 95, 90, 85, 80, 75, or less. In one embodiment, point A can be (26, 100), point B can be (26, 95), point C can be (10, 95), and point D can be (5, 100).

The invention also provides isolated nucleic acid molecules that are at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid having the sequence set forth in SEQ ID NO:1, 3, or 22. The hybridization conditions can be moderately or highly stringent hybridization conditions. Such nucleic acid molecules can be molecules that do not hybridize to the sense or antisense strand of a nucleic acid having the sequence set forth in SEQ ID NO:12 or 13.

For the purpose of this invention, moderately stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5×10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5×10^7$ cpm/µg), while the washes are performed at about 65° C. with a wash solution containing 0.2×SSC and 0.1% sodium dodecyl sulfate.

Isolated nucleic acid molecules within the scope of the invention can be obtained using any method including, without limitation, common molecular cloning and chemical nucleic acid synthesis techniques. For example, PCR can be used to obtain an isolated nucleic acid molecule containing a nucleic acid sequence sharing similarity to the sequences set forth in SEQ ID NO:1, 3, or 22. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Isolated nucleic acid molecules within the scope of the invention also can be obtained by mutagenesis. For example, an isolated nucleic acid containing a sequence set forth in SEQ ID NO:1, 3, or 22 can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain an isolated nucleic acid molecule within the scope of the invention. For example, any nucleic acid sequence having some homology to a sequence set forth in SEQ ID NO:1, 3, or 22, or any amino acid sequence having some homology to a sequence set forth in SEQ ID NO:2 can be used as a query to search GenBank®.

Further, nucleic acid hybridization techniques can be used to obtain an isolated nucleic acid molecule within the scope of the invention. Briefly, any nucleic acid molecule having some homology to a sequence set forth in SEQ ID NO:1, 3, or 22 can be used as a probe to identify a similar nucleic acid by hybridization under conditions of moderate to high stringency. Once identified, the nucleic acid molecule then can be purified, sequenced, and analyzed to determine whether it is within the scope of the invention as described herein.

Hybridization can be done by Southern or Northern analysis to identify a DNA or RNA sequence, respectively, that hybridizes to a probe. The probe can be labeled with a biotin, digoxygenin, an enzyme, or a radioisotope such as $^{32}$P. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence set forth in SEQ ID NO:1 or 3 can be used to identify an identical or similar nucleic acid. In addition, probes longer or shorter than 20 nucleotides can be used.

The invention provides isolated nucleic acid molecules that contain the entire nucleic acid sequence set forth in SEQ ID NO:1, 3, 4, 6, 8, 10, 17, 21, 22, or 23. In addition, the invention provides isolated nucleic acid molecules that contain a portion of the nucleic acid sequence set forth in SEQ ID NO:1, 3, or 22. For example, the invention provides an isolated nucleic acid molecule that contains a 15 nucleotide sequence identical to any 15 nucleotide sequence set forth in SEQ ID NO:1, 3, or 22 including, without limitation, the sequence starting at nucleotide number 1 and ending at nucleotide number 15, the sequence starting at nucleotide number 2 and ending at nucleotide number 16, the sequence starting at nucleotide number 3 and ending at nucleotide number 17, and so forth. It will be appreciated that the invention also provides isolated nucleic acid molecules that contain a nucleotide sequence that is greater than 15 nucleotides (e.g., 16, 17, 18, 19, 20, 21, 22, 23, 24, 25, 26, 27, 28, 29, 30, or more nucleotides) in length and identical to any portion of the sequence set forth in SEQ ID NO:1, 3, or 22. For example, the invention provides an isolated nucleic acid molecule that contains a 25 nucleotide sequence identical to any 25 nucleotide sequence set forth in SEQ ID NO:1, 3, or 22 including, without limitation, the sequence starting at nucleotide number 1 and ending at nucleotide number 25, the sequence starting at nucleotide number 2 and ending at nucleotide number 26, the sequence starting at nucleotide number 3 and ending at nucleotide number 27, and so forth. Additional examples include, without limitation, isolated nucleic acid molecules that contain a nucleotide sequence that is 50 or more nucleotides (e.g., 100, 150, 200, 250, 300, 350, or more nucleotides) in length and identical to any portion of the sequence set forth in SEQ ID NO:1, 3, or 22.

In addition, the invention provides isolated nucleic acid molecules that contain a variation of the nucleic acid sequence set forth in SEQ ID NO:1, 3, or 22. For example, the invention provides an isolated nucleic acid molecule containing a nucleic acid sequence set forth in SEQ ID NO:1, 3, or 22 that contains a single insertion, a single deletion, a single substitution, multiple insertions, multiple deletions, multiple substitutions, or any combination thereof (e.g., single deletion together with multiple insertions). The invention also provides isolated nucleic acid molecules that contain a variant of a portion of the nucleic acid sequence set forth in SEQ ID NO:1, 3, or 22 as described herein.

The invention provides isolated nucleic acid molecules that contain a nucleic acid sequence that encodes the entire amino acid sequence set forth in SEQ ID NO:2. In addition, the invention provides isolated nucleic acid molecules that contain a nucleic acid sequence that encodes a portion of the amino acid sequence set forth in SEQ ID NO:2. For example, the invention provides isolated nucleic acid molecules that contain a nucleic acid sequence that encodes a 5 amino acid sequence identical to any 5 amino acid sequence set forth in SEQ ID NO:2 including, without limitation, the sequence starting at amino acid residue number 1 and ending at amino acid residue number 5, the sequence starting at amino acid residue number 2 and ending at amino acid residue number 6, the sequence starting at amino acid residue number 3 and ending at amino acid residue number 7, and so forth. It will be appreciated that the invention also provides isolated nucleic acid molecules that contain a nucleic acid sequence that encodes an amino acid sequence that is greater than 5 amino acid residues (e.g., 6, 7, 8, 9, 10, 11, 12, 13, 14, 15, 16, 17, 18, 19, 20, 21, 22, 23, 24, 25, or more amino acid residues) in length and identical to any portion of the sequence set forth in SEQ ID NO:2. For example, the invention provides isolated nucleic acid molecules that contain a nucleic acid sequence that encodes a 15 amino acid sequence identical to any 15 amino acid sequence set forth in SEQ ID NO:2 including, without limitation, the sequence starting at amino acid residue number 1 and ending at amino acid residue number 15, the sequence starting at amino acid residue number 2 and ending at amino acid residue number 16, the sequence starting at amino acid residue number 3 and ending at amino acid residue number 17, and so forth. Additional examples include, without limitation, isolated nucleic acid molecules that contain a nucleic acid sequence that encodes an amino acid sequence that is 20 or more amino acid residues (e.g., 21, 22, 23, 24, 25, or more amino acid residues) in length and identical to any portion of the sequence set forth in SEQ ID NO:2.

In addition, the invention provides isolated nucleic acid molecules that contain a nucleic acid sequence that encodes an amino acid sequence having a variation of the amino acid sequence set forth in SEQ ID NO:2. For example, the invention provides isolated nucleic acid molecules containing a nucleic acid sequence encoding an amino acid sequence set forth in SEQ ID NO:2 that contains a single insertion, a single deletion, a single substitution, multiple insertions, multiple deletions, multiple substitutions, or any combination thereof (e.g., single deletion together with multiple insertions). The invention also provides isolated nucleic acid molecules containing a nucleic acid sequence encoding an amino acid sequence that contains a variant of a portion of the amino acid sequence set forth in SEQ ID NO:2 as described herein.

The isolated nucleic acid molecules within the scope of the invention can encode a polypeptide having mu3 opiate receptor activity. Any method can be use to determine whether or not a particular nucleic acid molecule encodes a polypeptide having mu3 opiate receptor activity. For example, cells transfected with a particular nucleic acid molecule can be analyzed to determine the expressed polypeptide's binding affinity for morphine and DAMGO. If the binding affinity for morphine is higher than the binding affinity for DAMGO, then the expressed polypeptide has mu3 opiate receptor activity. Controls can be used to confirm the specificity of the various binding affinities. For example, untranfected cells can be used to confirm that the measured binding affinity is specific for the polypeptide encoded by the introduced nucleic acid molecule. Examples of techniques that can be used to evaluate mu3 opiate receptor activities are provided elsewhere (e.g., WO99/24471).

Polypeptides

The invention provides substantially pure polypeptides. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel.

Any substantially pure polypeptide having an amino acid sequence encoded by a nucleic acid within the scope of the invention is itself within the scope of the invention. In addition, any substantially pure polypeptide containing an amino acid sequence having a length and a percent identity to the sequence set forth in SEQ ID NO:2 over that length as determined herein is within the scope of the invention provided the point defined by that length and percent identity is within the area defined by points A, B, C, and D of FIG. 1; where point A has an X coordinate less than or equal to 26, and a Y coordinate less than or equal to 100; where point B has an X coordinate less than or equal to 26, and a Y coordinate greater than or equal to 50; where point C has an X coordinate greater than or equal to 10, and a Y coordinate greater than or equal to 50; and where point D has an X coordinate greater than or equal to 5, and a Y coordinate less than or equal to 100. For example, the X coordinate for point A can be 26, 25, 24, 23, 22, 21, 20, or less; and the Y coordinate for point A can be 100, 99, 95, 90, 85, 80, 75, or less. The X coordinate for point B can be 26, 25, 24, 23, 22, 21, 20, or less; and the Y coordinate for point B can be 50, 55, 60, 65, 70, 75, 80, 85, 90, 95, 99 or more. The X coordinate for point C can be 10, 12, 14, 16, 17, 18, 20, or more; and the Y coordinate for point C can be 50, 55, 60, 65, 70, 75, 80, 85, 90, 95, 99 or more. The X coordinate for point D can be 5, 6, 7, 8, 9, 10, 15, 20, or more; and the Y coordinate for point D can be 100, 99, 95, 90, 85, 80, 75, or less. In one embodiment, point A can be (26, 100), point B can be (26, 95), point C can be (10, 95), and point D can be (5, 100).

Any method can be used to obtain a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, tissue from wild-type or transgenic animals can be used as a source material. In addition, tissue culture cells engineered to over-express a particular polypeptide of interest can be used to obtain substantially pure polypeptide. Further, a polypeptide within the scope of the invention can be engineered to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase.

The invention provides polypeptides that contain the entire amino acid sequence set forth in SEQ ID NO:2, 5, 7, or 9. In addition, the invention provides polypeptides that contain a portion of the amino acid sequence set forth in SEQ ID NO:2. For example, the invention provides polypeptides that contain a 5 amino acid sequence identical to any 5 amino acid sequence set forth in SEQ ID NO:2 including, without limitation, the sequence starting at amino acid residue number 1 and ending at amino acid residue number 5, the sequence starting at amino acid residue number 2 and ending at amino acid residue number 6, the sequence starting at amino acid residue number 3 and ending at amino acid residue number 7, and so forth. It will be appreciated that the invention also provides polypeptides that contain an amino acid sequence that is greater than 5 amino acid residues (e.g., 6, 7, 8, 9, 10, 11, 12, 13, 14, 15, 16, 17, 18, 19, 20, 21, 22, 23, 24, 25, or more amino acid residues) in length and identical to any portion of the sequence set forth in SEQ ID NO:2. For example, the invention provides polypeptides that contain a 15 amino acid sequence identical to any 15 amino acid sequence set forth in SEQ ID NO:2 including, without limitation, the sequence starting at amino acid residue number 1 and ending at amino acid residue number 15, the sequence starting at amino acid residue number 2 and ending at amino acid residue number 16, the sequence starting at amino acid residue number 3 and ending at amino acid residue number 17, and so forth. Additional examples include, without limitation, polypeptides that contain an amino acid sequence that is 20 or more amino acid residues (e.g., 21, 22, 23, 24, 25, or more amino acid residues) in length and identical to any portion of the sequence set forth in SEQ ID NO:2.

In addition, the invention provides polypeptides containing an amino acid sequence having a variation of the amino acid sequence set forth in SEQ ID NO:2. For example, the invention provides polypeptides containing an amino acid sequence set forth in SEQ ID NO:2 that contains a single insertion, a single deletion, a single substitution, multiple insertions, multiple deletions, multiple substitutions, or any combination thereof (e.g., single deletion together with multiple insertions). The invention also provides polypeptides containing an amino acid sequence that contains a variant of a portion of the amino acid sequence set forth in SEQ ID NO:2 as described herein.

The substantially pure polypeptides within the scope of the invention can have mu3 opiate receptor activity. Any method can be use to determine whether or not a particular polypeptide has mu3 opiate receptor activity. For example, cells expressing a particular polypeptide can be analyzed to determine the polypeptide's binding affinity for morphine and DAMGO. If the binding affinity for morphine is higher than the binding affinity for DAMGO, then the expressed polypeptide has mu3 opiate receptor activity. Controls can be used to confirm the specificity of the various binding affinities. For example, cells lacking the polypeptide can be used to confirm that the measured binding affinity is specific for that particular polypeptide.

Host Cells

A host cell within the scope of the invention is any cell containing at least one isolated nucleic acid molecule described herein. Such cells can be prokaryotic and eukaryotic cells. It is noted that cells containing an isolated nucleic acid molecule within the scope of the invention are not required to express a polypeptide. In addition, the isolated nucleic acid molecule can be integrated into the genome of the cell or maintained in an episomal state. Thus, host cells can be stably or transiently transfected with a construct containing an isolated nucleic acid molecule of the invention.

Host cells within the scope of the invention can contain an exogenous nucleic acid molecule that encodes a polypeptide having mu3 opiate receptor activity. Such host cells can express the encoded polypeptide such that the host cells exhibit at least one mu3 opiate receptor-mediated response after treatment with a mu3 opiate receptor agonist.

Any methods can be used to introduce an isolated nucleic acid molecule into a cell in vivo or in vitro. For example, calcium phosphate precipitation, electroporation, heat shock, lipofection, microinjection, and viral-mediated nucleic acid transfer are common methods that can be used to introduce an isolated nucleic acid molecule into a cell. In addition, naked DNA can be delivered directly to cells in vivo as describe elsewhere (U.S. Pat. Nos. 5,580,859 and 5,589,466 including continuations thereof). Further, isolated nucleic acid molecules can be introduced into cells by generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce isolated nucleic acid molecules into animals to produce the founder lines of transgenic animals. Such techniques include, without limitation, pronuclear microinjection (U.S. Pat. No. 4,873,191); retrovirus mediated gene transfer into germ lines (Van der Putten et al., *Proc. Natl. Acad. Sci., USA*, 82:6148 (1985)); gene transfection into embryonic stem cells (Gossler A et al., *Proc Natl Acad Sci USA* 83:9065-9069 (1986)); gene targeting into embryonic stem cells (Thompson et al., *Cell,* 56:313 (1989)); nuclear transfer of somatic nuclei (Schnieke A E et al., *Science* 278:2130-2133 (1997)); and electroporation of embryos (Lo C W, *Mol. Cell. Biol.,* 3:1803-1814 (1983)). Once obtained, transgenic animals can be replicated using traditional breeding or animal cloning.

Any methods can be used to identify cells containing an isolated nucleic acid molecule of the invention. Such methods include, without limitation, PCR and nucleic acid hybridization techniques such as Northern and Southern analysis. In some cases, immunohistochemistry and biochemical techniques can be used to determine if a cell contains a particular isolated nucleic acid molecule by detecting the expression of a polypeptide encoded by that particular nucleic acid molecule.

Identifying mu3 Opiate Receptor Agonists

A mu3 opiate receptor agonist is any molecule that interacts with a polypeptide having mu3 opiate receptor activity such that a mu3 opiate receptor-mediated response is induced. Mu3 opiate receptor-mediated responses include, without limitation, changes in intracellular calcium concentration and nitric oxide release.

Mu3 opiate receptor agonists can be identified by (1) contacting cells expressing a polypeptide having mu3 opiate receptor activity with a test molecule, and (2) determining if that test molecule induces a mu3 opiate receptor-mediated response. Such cells include cells expressing a polypeptide having mu3 opiate receptor activity (e.g., heart cells, vein cells, artery cells, testicular cells, and white blood cells) as well as cells containing an isolated nucleic acid molecule that expresses a polypeptide having mu3 opiate receptor activity. For example, a mu3 opiate receptor agonist can be identified by contacting cells containing an isolated nucleic acid molecule having a sequence as set forth in SEQ ID NO:4, 6, 8, or 10 with a test molecule, and determining if that test molecule induces changes in intracellular calcium concentration in a mu3-specific manner. The specificity of the interaction between a potential mu3 opiate receptor agonist and a mu3 opiate receptor can be determined using a known mu3 opiate receptor antagonist. For example, a test molecule that induces a change in intracellular calcium concentration can be identified as a mu3 opiate receptor agonist if a mu3 opiate receptor antagonist can inhibit the induction of that change in intracellular calcium concentration. In addition, the specificity of agonist-receptor interactions can be demonstrated using heterologous expression systems, receptor binding analyses, or any other method that provides a measure of agonist-receptor interaction.

A test molecule can be any molecule having any chemical structure. For example, a test molecule can be a polypeptide, carbohydrate, lipid, amino acid, nucleic acid, fatty acid, or steroid. In addition, a test molecule can be lipophilic, hydrophilic, plasma membrane permeable, or plasma membrane impermeable.

The invention provides several assays that can be used to identify a mu3 opiate receptor agonist. Such assays involve monitoring at least one of the biological responses mediated by a mu3 opiate receptor in cells expressing a polypeptide having mu3 opiate receptor activity such as cells containing an exogenous nucleic acid molecule that expresses a polypeptide having mu3 opiate receptor activity. As described herein, mu3 opiate receptor-mediated responses include, without limitation, increases in intracellular calcium concentration and nitric oxide release. Thus, a mu3 opiate receptor agonist can be identified using an assay that monitors intracellular calcium concentration, nitric oxide release, or both in cells transfected with a nucleic acid molecule that expresses a polypeptide having mu3 opiate receptor activity.

Intracellular calcium concentrations can be monitored using any method. For example, intracellular calcium concentrations can be monitored using a dye that detects calcium ions. In this case, cells can be loaded with a fluorescent dye (e.g., fura-2) and monitored by dual emission microfluorimetry. The fura-2 loading process can involve washing the cells (e.g., one to four times) with incubation medium lacking calcium. This medium can be balanced with sucrose to maintain osmolarity. After washing, the cells can be incubated (e.g., 30 minutes) with loading solution. This loading solution can contain, for example, 5 µM fara-2/AM and a non-ionic/non-denaturing detergent such as Pluronic F-127. The non-ionic/non-denaturing detergent can help disperse the acetoxymethyl (AM) esters of fura-2. After incubation with the loading solution, the cells can be washed (e.g., one to four times) with, for example, PBS without calcium or magnesium to remove extracellular dye.

Once loaded, the intracellular calcium concentration ($[Ca^{2+}]i$) can be calculated from the fluorescence ratio (340 and 380 nm excitation and 510 nm emission wavelength) according to the following equation: $[Ca^{2+}]i=(R-R_{min})k_d\beta/(R_{max}-R)$; where R=fluorescence ratio recorded from the cell; $R_{min}$=fluorescence ratio of fura-2 free acid recorded in absence of $Ca^{2+}$; $R_{max}$=fluorescence ratio of fura-2 free acid recorded in saturating concentration of $Ca^{2+}$; $k_d$=calcium dissociation constant of the dye; and β=the ratio of fluorescence of fura-2 free acid in the $Ca^{2+}$ free form to the $Ca^{2+}$ saturated form recorded at the wavelength used in the denominator of the ratio. Using an image processing system such as a COMPIX C-640 SIMCA (Compix Inc., Mars, Pa.) system with an inverted microscope, images can be acquired for analysis every 0.4 seconds.

Nitric oxide (NO) release can be monitored directly or indirectly using any method. For example, a NO-specific amperometric probe can be used to measure directly the NO released from cultured cells or tissue fragments as described elsewhere (Stefano G B et al., *J. Biol. Chem.* 270:30290 (1995) and Magazine H L et al., *J. Immunol.* 156:4845 (1996)). Using this NO-specific probe, the concentration of NO gas in solution can be measured in real-time with, for example, a DUO 18 computer data acquisition system obtained from World Precision Instruments. Briefly, the cells or tissue fragments can be placed in a superfusion chamber containing, for example, 2 mL PBS. In addition, a micromanipulator (e.g., a micromanipulator obtained from Zeiss-Eppendorff) can be attached to the stage of an inverted microscope to aid in positioning the amperometric probe 15 µm above the surface of a cell or tissue fragment. Prior to obtaining measurements, the amperometric probe can be calibrated by generating a standard curve using different concentrations of a nitrosothiol donor such as S-nitroso-N-acetyl-DL-penicillamine (SNAP) obtained from Sigma (St. Louis, Mo.). In addition, the amperometric probe can be equilibrated in the same solution (e.g., PBS) used to incubate the cells or tissue fragments during analysis.

Identifying mu3 Opiate Receptor Antagonists

A mu3 opiate receptor antagonist is any molecule that interacts with a polypeptide having mu3 opiate receptor activity such that the induction of a mu3 opiate receptor-mediated response is inhibited or prevented. A mu3 opiate receptor antagonist can be identified by (1) contacting cells expressing a polypeptide having mu3 opiate receptor activity with a mu3 opiate receptor agonist and a test molecule, and (2) determining if that test molecule inhibits the mu3 opiate receptor agonist from inducing a mu3 opiate receptor-mediated response. Such cells include cells expressing a polypeptide having mu3 opiate receptor activity (e.g., heart cells, vein cells, artery cells, testicular cells, and white blood cells) as well as cells containing an isolated nucleic acid molecule that expresses a polypeptide having mu3 opiate receptor activity. For example, a mu3 opiate receptor antagonist can be identified by (1) contacting cells transfected with a nucleic acid molecule that expresses a polypeptide having mu3 opiate receptor activity with morphine and a test molecule, and (2) determining if that test molecule inhibits morphine from inducing nitric oxide release. Again, a test molecule can be any molecule having any chemical structure. For example, a test molecule can be a polypeptide, carbohydrate, lipid, amino acid, nucleic acid, fatty acid, or steroid. In addition, a test molecule can be lipophilic, hydrophilic, plasma membrane permeable, or plasma membrane impermeable. The cells can be contacted with the test molecule and the mu3 opiate receptor agonist in any order. For example, the test molecule can be added before the mu3 opiate receptor agonist, the test molecule can be added after the mu3 opiate receptor agonist, or the test molecule and mu3 opiate receptor agonist can be added simultaneously.

It is to be understood that each of the assays for identifying mu3 opiate receptor agonists described herein can be adapted such that mu3 opiate receptor antagonists can be identified.

The invention will be further described in the following examples, which do not limit the scope of the invention described in the claims.

EXAMPLES

Example 1

Nucleic Acid Encoding a Polypeptide Having mu3 Opiate Receptor Activity

A human testis cDNA library constructed in the pEXP1 mammalian expression vector was obtained from Clonetech (Palo Alto, Calif.). After obtaining a DNA sample from the human testis cDNA library, the library was prescreened by PCR using primers designed to amplify a 441 base pair region of the human mu1 opioid receptor. The forward primer had a sequence corresponding to position 892-919 of the human mu1 opioid receptor (5'-GGTACTGGGAAAAC-CTGCTGAAGATCTG-3'; SEQ ID NO:14), and the reverse primer had a sequence corresponding to position 1305-1332 of the human mu1 opioid receptor (5'-GGTCTCTAGTGT-TCTGACGAATTCGAGT-3'; SEQ ID NO:15). After the amplification reaction, the amplification products were separated by gel electrophoresis using a 2% agarose gel stained with ethidium bromide. A 441 base pair fragment was observed.

The human testis cDNA library was screened with a probe made using the same forward and reverse primers. Briefly, the screen was performed using ClonCapture cDNA Selection Kit (CloneTech; Palo Alto, Calif.) according to the manufacturer's instructions. Two positive colonies were identified in the enrichment library screen. PCR confirmed that the two colonies were positive. After isolation, the plasmid DNA from the two colonies was digested with SfiI and separated by gel electrophoresis. One insert was found to be about 1.1 kb in size while the other was found to be about 2.0 kb in size. Each insert was sequenced.

Sequence analysis of the 2.0 kb insert revealed a new splice variant that replaces the last 12 amino acid residues of the human mu1 opioid receptor with 26 different amino acid residues. Specifically, the nucleic acid sequence that encodes the LENLEAETAPLP (SEQ ID NO:16) carboxyl-terminus sequence of the mu1 opioid receptor was found to be replaced with a nucleic acid sequence that encodes NYYIIHRLCCNTPLISQKPVLLWFCD (SEQ ID NO:2). The nucleic acid sequence encoding NYYIIHRLCCNTPLISQKPVLLWFCD (SEQ ID NO:2) was found to be 5'-AATTATTATATAATTCATAGATGTTGCTGCAATACCCCTCTTATTTCTCAAAAGCCAGTCTTGCTCT GGTTCTGTGATTAA-3' (SEQ ID NO:1). The following nucleic acid sequence contains the sequence set forth in SEQ ID NO:1 as well as the sequence found to extend past the TAA stop codon: 5'-AATTATTATATAATTCATAGATGTTGCTGCAATACCCCTCTTATTTCTCAAAAGCCAGTCTTGCTCTGGTTCTGTGATTAAAGAGAGGGTGAGTGCCTTGCCCACTGTGTCATGGATGCAAGATATTCACAG AAAATTAGCATCATAGAAAAAAANAAAAAAAAAAAAAAANCATGTCGGCCGCCTCGGCCAAACATCGGGTCGAGCATGCATCTAGGGCGGCCAATTC CGCCCCTCTCCCCCCNGCNNTTT (SEQ ID NO:3). This sequence was found to replace the sequence of SEQ ID NO:12 that corresponds to nucleotide number 1374-1826 as follows: 5'-CTAGAAAATCTGGAAGCAGAAACTGCTCCGTTGCCCTAACAGGGTCTCATGCCATTCCGACCTTCACCAAGCTTAGAAGCCACCATGTATGTGGAA GCAGGTTGCTTCAAGAATGTGTAGGAGGCTCTAATTCTCTAGGAAAGTGCCT GCTTTTAGGTCATCCAACCTCTTTCCTCTCTGGCCACTCTGCTCTGCACATTAG AGGGACAGCCAAAAGTAAGTGGAGCATTTGGAAGGAAAGGAATATACCACA CCGAGGAGTCCAGTTTGTGCAAGACACCCAGTGGAACCAAAACCCATCGTGG TATGTGAATTGAAGTCATCATAAAAGGTGACCCTTCTGTCTGTAAGATTTTAT TTTCAAGCAAATATTTATGACCTCAACAAAGAAGAACCATCTTTTGTTAAGTT CACCGTAGTAACACATAAAGTAAATGCTACCTCTGATCAAAG-3' (SEQ D NO:18).

The following nucleic acid sequence encodes a polypeptide that uses the start codon of the human mu1 opioid receptor and the carboxyl-terminus of the 2.0 kb insert: 5'-ATGTCAGATGCTCAGCTCGGTCCCCTCCGCCTGACGCTCCTCTCTGTCTCAGCCAGGACTGGTTTCTGTAAGAAACAGCAGGAGCTGTGGCAGCGGCGAA AGGAAGCGGCTGAGGCGCTTGGAACCCGAAAAGTCTCGGTGCTCCTGGCTAC CTCGCACAGCGGTGCCCGCCCGGCCGTCAGTACCATGGACAGCAGCGCTGCC CCCACGAACGCCAGCAATTGCACTGATGCCTTGGCGTACTCAAGTTGCTCCCC AGCACCCAGCCCCGGTTCCTGGGTCAACTTGTCCCACTTAGATGGCAACTGT CCGACCCATGCGGTCCGAACCGCACCGACCTGGGCGGGAGAGACAGCCTGTG CCCTCCGACCGGCAGTCCCTCCATGATCACGGCCATCACGATCATGGCCCTCT ACTCCATCGTGTGCGTGGTGGGGCTCT TCGGAAACTTCCTGGTCATGTATGTG ATTGTCAGATACACCAAGATGAAGACTGCCACCAACATCTACATTTTCAACCT TGCTCTGGCAGATGCCTTAGCCACCAGTACCCTGCCCTTCCAGAGTGTGAATT ACCTAATGGGAACATGGCCATTTGGAACCATCCTTTGCAAGATAGTGATCTCC ATAGATTACTATAACATGTTCACCAGCATATTCACCCTCTGCACCATGAGTGT TGATCGATACATTGCAGTCTGCCACCCTGTCAAGGCCTTAGATTTCCGTACTC CCCGAAATGCCAAAATTATCAATGTCTGCAACTGGATCCTCTCTTCAGCCATT GGTCTTCCTGTAATGTTCATGGCTACAACAAAATACAGGCAAGGTTCCATAG ATTGTACACTAACATTCTCTCATCCAACCTGGTACTGGGAAAACCTGCTGAAG ATCTGTGTTTTCATCTTCGCCTTCATTATGCCAGTGCTCATCATTACCGTGTGC TATGGACTGATGATCTTGCGCCTCAAGAGTGTCCGCATGCTCTCTGGCTCCAA AGAAAAGGACAGGAATCTTCGAAGGATCACCAGGATGGTGCTGGTGGTTGGCTGTGTTCATCGTCTGCTGGACTCCCATTCACATTTACGTCATCATTAAAG CCTTGGTTACAATCCCAGAAACTACGTTCCAGACTGTTTCTTGGCACTTCTGC ATTGCTCTAGGTTACACAAACAGCTGCCTCAACCCAGTCCTTTATGCATTTCT GGATGAAAACTTCAAACGATGCTTCAGAGAGTTCTGTATCCCAACCTCTTCCA ACATTGAGCAACAAAACTCCACTCGAATTCGTCAGAACACTAGAGACCACCC CTCCACGGCCAATACAGTGGATAGAACTAATCATCAGAATTATTATATAATTC ATAGATGTTGCTGCAATACCCCTCTTATTTCTCAAAAGCCAGTCTTGCTCTGG TTCTGTGATTAA-3' (SEQ ID NO:6). The amino acid sequence encoded by this nucleic acid sequence is as follows: MSDAQLGPLRLTLLSVSARTGFCKKQQELWQRRKEAAEALGTRKVSVLLATSHSGARPAVSTMDSSAAPTNASNCTDALAYS SCSPAPSPGSWVNLSHLDGNLSDPCGPNRTDLGGRDSLCPPTGSPSMITAITIMAL YSIVCVVGLFGNFLVMYVIVRYTKMKTATNIYIFNLALADALATSTLPFQSVNYL MGTWPFGTILCKIVISIDYYNMFTSIFTLCTMSVDRYIAVCHPVKALDFRTPRNAK IINVCNWILSSAIGLPVMFMATTKYRQGSIDCTLTFSHPTWYWENLLKICVFIFAFI MPVLIITVCYGLMILRLKSVRMLSGSKEKDRNLRRITRMVLVVVAVFIVCWTPIHI YVIIKALVTIPETTFQTVSWHFCIALGYTNSCLNPVLYAFLDENFKRCFREFCIPTS SNEEQQNSTRIRQNTRDHPSTANTVDRTNHQNYYIIHRLCCNTPLISQKPVLLWFC D (SEQ ID NO:7).

The following nucleic acid sequence encodes a polypeptide that uses the start codon of the human mu2 opioid receptor and the carboxyl-terminus of the 2.0 kb insert: 5'-ATGGACAGCAGCGCTGCCCCCACGAACGCCAGCAATTGCACTGATGCCTTGGCGTACTCAAGTTGCTCCCCAGCACCCAGCCCCGGTTCCTGGGTCAACT TGTCCCACTTAGATGGCAACTGTCGACCCATGCGGTCCGAACCGCACCGA CCTGGGCGGGAGAGACAGCCTGTGCCCTCCGACCGGCAGTCCCTCCATGATC ACGGCCAT CACGATCATGGCCCTCTACTCCATCGTGTGCGTGGTGGGGCTCTTCGGAAACTTCCTGGTCATGTATGTGATTGTCAGATACACCAAGATGAAGACT GCCACCAACATCTACATTTTCAACCTTGCTCTGGCAGATGCCTTAGCCACCAGTACCCTGCCCTTCCAGAGTGTGAATTACCTAATGGGAACATGGCCATTTGGAA CCATCCTTTGCAAGATAGTGATCTCCATAGATTACTATAACATGTTCACCAGCATATTCACCCTCTGCACCATGAGTGTTGATCGATACATTGCAGTCTGCCACCC TGTCAAGGCCTTAGATTTCCGTACTCCCCGAAATGCCAAAATTATCAATGTCTGCAACTGGATCCTCTCTTCAGCCATTGGTCTTCCTGTAATGTTCATGGCTACA ACAAAATACAGGCAAGGTTCCATAGATTGTACACTAACATTCTCTCATCCAACCTGGTACTGGGAAAACCTGCTGAAGATCTGTGTTTTCATCTTCGCCTTCATT ATGCCAGTGCTCATCATTACCGTGTGCTATGGACTGATGATCTTGCGCCTCAAGAGTGTCCGCATGCTCTCTGGCTCCAAAGAAAAGGACAGGAATCTTCGAAGG ATCACCAGGATGGTGCTGGTGGTGGTGGCTGTGTTCATCGTCTGCTGGACTCCCATTCACATTTACGTCATCATTAAAGCCTTGGTTACAATCCCAGAAACTACGT TCCAGACTGTTTCTTGGCACTTCTGCATTGCTCTAGGTTACACAAACAGCTGCCTCAACCCAGTCCTTTATGCATTTCTGGATGAAAACTTCAAACGATGCTTCAG AGAGTTCTGTATCCCAACCTCTTCCAACATTGAGCAACAAAACTCCACTCGAATTCGTCAGAACACTAGAGACCACCCCTCCACGGCCAATACAGTGGATAGAA CTAATCATCAGAATTATTATATAATTCATAGATGTTGCTGCAATACCCCTCTTATTTCTCAAAAGCCAGTCTTGCTCTGGTTCTGTGATTAA-3' (SEQ ID NO:8). The amino acid sequence encoded by this nucleic acid sequence is as follows: MDSSAAPTNASNCTDALAYSSCSPAPSPGSWVNLSHLDGNLSDPCGPNRTDLGGRDSLCPPTGSPSMITAITIMALYSIVCVVGLFGNFLVMYVIVRYTKMKTATNIYIFNLA LADALATSTLPFQSVNYLMGTWPFGTILCKIVISIDYYNMFTSIFTLCTMSVDRYIAVCHPVKALDFRTPRNAKIINVCNWILSSAIGLPVMFMATTKYRQGSIDCTLTFS HPTWYWENLLKICVFIFAFIMPVLIITVCYGLMILRLKSVRMLSGSKEKDRNLRRITRMVLVVVAVFIVCWTPIHIYVIIKALVTIPETTFQTVSWHFCIALGYTNSCLNPVLYAFLDENFKRCFREFCIPTSSNIEQQNSTRIRQNTRDHPSTANTVDRTNHQNYYII HRLCCNTPLISQKPVLLWFCD (SEQ ID NO:9).

The following nucleic acid sequence encodes a polypeptide that uses the start codon of the rat mu2 opioid receptor and the carboxyl-terminus of the 2.0 kb insert: 5'-ATGGACAGCAGCACCGGCCCAGGGAACACCAGCGACTGCTCAGACCCCTTAG CTCAGGCAAGTTGCTCCCCAGCACCTGGCTCCTGGGTCAACTTGTCCCACTTAGATGGCAACCTGTCCGACCCATGCGGTCCGAACCGCACCGACCTGGGCGGGA GAGACAGCCTGTGCCCTCCGACCGGCAGTCCCTCCATGATCACGGCCATCACGATCATGGCCCTCTACTCCATCGTGTGT GCGTGGTGGGGCTCTTCGGAAACTTCC TGGTCATGTATGTGATTGTCAGATACACCAAGATGAAGACTGCCACCAACATCTACATTTTCAACCTTGCTCTGGCAGATGCCTTAGCCACCAGTACCCTGCCCT TCCAGAGTGTGAATTACCTAATGGGAACATGGCCATTTGGAACCATCCTTTGCAAGATAGTGATCTCCATAGATTACTATAACATGTTCACCAGCATATTCACCCT CTGCACCATGAGTGTTGATCGATACATTGCAGTCTGCCACCCTGTCAAGGCCTTAGATTTCCGTACTCCCCGAAATGCCAAAATTATCAATGTCTGCAACTGGATC CTCTCTTCAGCCATTGGTCTTCCTGTAATGTTCATGGCTACAACAAAATACAGGCAAGGTTCCATAGATTGTACACTAACATTCTCTCATCCAACCTGGTACTGGG AAAACCTGCTGAAGATCTGTGTTTTCATCTTCGCCTTCATTATGCCAGTGCTCATCATTACCGTGTGCTATGGACTGATGATCTTGCGCCTCAAGAGTGTCCGCAT GCTCTCTGGCTCCAAAGAAAAGGACAGGAATCTTCGAAGGATCACCAGGATGGTGCTGGTGGTGGTGGCTGTGTTCATCGTCTGCTGGACTCCCATTCACATTTA CGTCATCATTAAAGCCTTGGTTACAATCCCAGAAACTACGTTCCAGACTGTTTCTTGGCACTTCTGCATTGCTCTAGGTTACACAAACAGCTGCCTCAACCCAGTC CTTTATGCATTTCTGGATGAAAACTTCAAACGATGCTTCAGAGAGTTCTGTATCCCAACCTCTTCCAACATTGAGCAACAAAACTCCACTCGAATTCGTCAGAAC ACTAGAGACCACCCCTCCACGGCCAATACAGTGGATAGAACTAATCATCAGAATTATTATATAATTCATAGATGTTGCTGCAATACCCCTCTTATTTCTCAAAAG CCAGTCTTGCTCTGGTTCTGTGATTAA-3' (SEQ ID NO:10). The amino acid sequence encoded by this nucleic acid sequence is as follows: MDSSTGPGNTSDCSDPLAQASCSPAPGSWVNLSHLDGNLSDPCGPNRTDLGGRDSLCPPTGSPSMIT AITIMALYSIVCVVGLFGNFLVMYVIVRYTKMKTATNIYIFNLALADALATSTLPFQSVNYLMGTWPFGTILCKIVISIDYYNMFTSIFTLCTMSVDRYIAVCHPVKALDFR TPRNAKIINVCNWILSSAIGLPVMFMATTKYRQGSIDCTLTFSHPTWYWENLLKIC VFIFAFIMPVLIITVCYGLMILRLKSVRMLSGSKEKDRNLRRITRMVLVVVAVFIV CWTPIHIYVIIKALVTIPETTFQTVSWHFCIALGYTNSCLNPVLYAFLDENFKRCFR EFCIPTSSNIEQQNSTRIRQNTRDHPSTANTVDRTNHQNYYIIHRLCCNTPLISQKP VLLWFCD (SEQ ID NO:11).

In addition, sequence analysis revealed that the 2.0 kb insert lacked the first exon of the human mu1 opioid receptor. Specifically, the 5' end of the 2.0 kb insert started with 5'-ATACACCAAGATG-3' (SEQ ID NO:17), lacking the first 498 nucleotides of the mu1 opioid receptor nucleic acid sequence reported in GenBank® accession number XM_004341, which is set forth in SEQ ID NO:12. The following nucleic acid sequence corresponds to the open reading frame of the 2.0 kb insert: 5'-ATGAAGACTGCCACCAACATCTACATTTTCAACCTTGCTCTGGCAGATGCCTTAGCCACCAGTACC CTGCCCTTCCAGAGTGTGAATTACCTAATGGGAACATGGCCATTTGGAACCAT CCTTTGCAAGATAGTGATCTCCATAGAT- TACTATAACATGTTCACCAGCATAT TCACCCTCTG-
CACCATGAGTGTTGATCGATACATTG-
CAGTCTGCCACCCTGTC
AAGGCCTTAGATTTCCGTACTC-
CCCGAAATGCCAAAATTATCAATGTCTGCAA CTG-
GATCCTCTCTTCAGCCATTGGTCTTCCT-
GTAATGTTCATGGCTACAACAA
AATACAGGCAAGGTTCCATAGATTGTA-
CACTAACATTCTCTCATCCAACCTGG TACTGG-
GAAAACCTGCTGAAGATCTGT-
GTTTTCATCTTCGCCTTCATTATGCC
AGTGCTCATCATTACCGTGTGCTATG-
GACTGATGATCTTGCGCCTCAAGAGTG TCCGCAT-
GCTCTCTGGCTCCAAAGAAAAGGACAG-
GAATCTTCGAAGGATCAC
CAGGATGGTGCTGGTGGTGGTGGCTGT-
GTTCATCGTCTGCTGGACTCCCATTC ACATTTACGT-
CATCATTAAAGCCTTGGTTACAATCCCA-
GAAACTACGTTCCAG
ACTGTTTCTTGGCACTTCTGCAT-
TGCTCTAGGTTACACAAACAGCTGCCTCAA
CCCAGTCCTTTATGCATTTCTGGAT-
GAAAACTTCAAACGATGCTTCAGAGAGT TCTG-
TATCCCAACCTCTTCCAACATTGAGCAA-
CAAAACTCCACTCGAATTCGT
CAGAACACTAGAGACCACCCCTCCACG-
GCCAATACAGTGGATAGAACTAATC ATCAGAAT-
TATTATATAATTCATAGATGTTGCTG-
CAATACCCCTCTTATTTCTC
AAAAGCCAGTCTTGCTCTGGTTCTGTGATTAA (SEQ
ID NO:4). The amino acid sequence encoded by this open
reading frame is as follows: MKTATNIYIFNLALAD-
ALATSTLPFQSVNYLMGTWPFGTILCKIVISIDYYN-
MFTSIFTLCTMSVDRYIAVC HPVKALDFRTPRNAKI-
INVCNWILSSAIGLPVMFMATTKYRQG-
SIDCTLTFSHPT WYWENLLKICVFIFAFIMPVLIITV-
CYGLMILRLKSVRMLSGSKEKDRNLRRITRM
VLVVVAVFIVCWTPIHIYVIIKALVTI-
PETTFQTVSWHFCIALGYTNSCLNPVLYAF LDEN-
FKRCFREFCIPTSSNIEQQNSTRIRQN-
TRDHPSTANTVDRTNHQNYYIIHRLC
CNTPLISQKPVLLWFCD (SEQ ID NO:5).

The nucleic acid sequence reported for the human mu1
opioid receptor is as follows: 5'-GAGGGGGCTATACGCA-
GAGGAGAATGTCAGATGCTCAGCTCG-
GTCCCCTCCGCCTGACGCTCCTCTCT-
GTCTCAGCCAGGACTGGTTTCTGTAAGAA
ACAGCAGGAGCTGTGGCAGCGGCGAAAG-
GAAGCGGCTGAGGCGCTTGGAAC
CCGAAAAGTCTCGGTGCTCCTGGCTAC-
CTCGCACAGCGGTGCCCGCCCGGCC GTCAGTAC-
CATGGACAGCAGCGCTGCCCCCAC-
GAACGCCAGCAATTGCACTG
ATGCCTTGGCGTACTCAAGTTGCTC-
CCCAGCACCCAGCCCCGGTTCCTGGGTC AACT-
TGTCCCACTTAGATGGCAACCTGTC-
CGACCCATGCGGTCCGAACCGCA
CCGACCTGGGCGGGAGAGACAGCCTGT-
GCCCTCCGACCGGCAGTCCCTCCAT GATCACGGC-
CATCACGATCATGGCCCTCTACTC-
CATCGTGTGCGTGGTGGGG
CTCTTCGGAAACTTCCTGGTCATGTAT-
GTGATTGTCAGATACACCAAGATGAA GACTGC-
CACCAACATCTACATTTTCAACCT-
TGCTCTGGCAGATGCCTTAGCCA
CCAGTACCCTGCCCTTCCAGAGTGT-
GAATTACCTAATGGGAACATGGCCATTT GGAAC-
CATCCTTTGCAAGATAGTGATCTCCATA-
GATTACTATAACATGTTCAC
CAGCATATTCACCCTCTGCACCATGAGT-
GTTGATCGATACATTGCAGTCTGCC ACCCTGT-
CAAGGCCTTAGATTTCCGTACTC-
CCCGAAATGCCAAAATTATCAAT
GTCTGCAACTGGATCCTCTCTTCAGC-
CATTGGTCTTCCTGTAATGTTCATGGCT ACAA-
CAAAATACAGGCAAGGTTCCATAGATTG-
TACACTAACATTCTCTCATC
CAACCTGGTACTGGGAAAACCTGCTGAA-
GATCTGTGTTTTCATCTTCGCCTTC ATTATGCCAGT-
GCTCATCATTACCGTGTGCTATGGACT-
GATGATCTTGCGCCT
CAAGAGTGTCCGCATGCTCTCTGGCTC-
CAAAGAAAAGGACAGGAATCTTCGA AGGATCAC-
CAGGATGGTGCTGGTGGTGGTGGCTGT-
GTTCATCGTCTGCTGGA
CTCCCATTCACATTTACGTCATCAT-
TAAAGCCTTGGTTACAATCCCAGAAACT ACGTTC-
CAGACTGTTTCTTGGCACTTCTGCAT-
TGCTCTAGGTTACACAAACAG
CTGCCTCAACCCAGTCCTTTATG-
CATTTCTGGATGAAAACTTCAAACGATGCT TCA-
GAGAGTTCTGTATCCCAACCTCTTCCAA-
CATTGAGCAACAAAACTCCACT
CGAATTCGTCAGAACACTAGAGACCAC-
CCCTCCACGGCCAATACAGTGGATA GAACTAAT-
CATCAGCTAGAAAATCTGGAAGCA-
GAAACTGCTCCGTTGCCCTA
ACAGGGTCTCATGCCATTCCGACCT-
TCACCAAGCTTAGAAGCCACCATGTAT GTGGAAG-
CAGGTTGCTTCAAGAATGTGTAGGAG-
GCTCTAATTCTCTAGGAAA
GTGCCTGCTTTTAGGTCATCCAAC-
CTCTTTCCTCTCTGGCCACTCTGCTCTGCA CATTA-
GAGGGACAGCCAAAAGTAAGTGGAG-
CATTTGGAAGGAAAGGAATAT
ACCACACCGAGGAGTCCAGTTTGTGCAA-
GACACCCAGTGGAACCAAAACCCA TCGTGGTAT-
GTGAATTGAAGTCATCATAAAAGGTGAC-
CCTTCTGTCTGTAAGA
TTTTATTTTCAAGCAAATATTTATGAC-
CTCAACAAAGAAGAACCATCTTTTGT TAAGT-
TCACCGTAGTAACACATAAAGTAAATGC-
TACCTCTGATCAAAGCACC
TTGAATGGAAGGTCCGAGTCTTTTTAGT-
GTTTTGCAAGGGAATGAATCCATTA TTCTATTTTA-
GACTTTTAACTTCACCTTAAAATTAG-
CATCTGGCTAAGGCATC
ATTTTCACCTCCATTTCTTGGTTTTG-
TATTGTTTAAAAAAATAACATCTCTTTC
ATCTAGCTCCATAATTGCAAGGGAA-
GAGATTAGCATGAAAGGTAATCTGAAA CACAGT-
CATGTGTCAGCTGTAGAAAGGTTGAT-
TCTCATGCACTGCAAATACTT
CCAAAGAGTCATCATGGGG-
GATTTTTCATTCTTAGGCTTTCAGTGGTTTGTTC C-3'
(SEQ ID NO:12).

The nucleic acid sequence reported for the human mu2
opioid receptor is as follows: 5'-GCAGAGGAGAATGT-
CAGATGCTCAGCTCGGTCCCCTCCGCCT-
GACGCTCCTCTCTGTCTCAGCCAG-
GACTGGTTTCTGTAAGAAACAGCAGGAGCTG
TGGCAGCGGCGAAAGGAAGCGGCTGAG-
GCGCTTGGAACCCGAAAAGTCTCG GTGCTCCTG-
GCTACCTCGCACAGCGGTGCCCGCCCG- GCCGTCAGTACCATGG ACAGCAGCGCTGCCCCCACGAACGCCAG-CAATTGCACTGATGCCTTGGCGTA CTCAAGT-TGCTCCCCAGCACCCAGCCCCGGTTC-CTGGGTCAACTTGTCCCACT TAGATGGCGACCTGTCCGACCCATGCG-GTCCGAACCGCACCGACCTGGGCGG GAGAGA-CAGCCTGTGCCCTCCAACCGGCAGTC-CCTCCATGATCACGGCCATC ACGATCATGGCCCTCTACTCCATCGTGT-GCGTGGTGGGGCTCTTCGGAAACTT CCTGGTCAT-GTATGTGATTGTCAGATACACCAAGAT-GAAGACTGCCACCAAC ATCTACATTTTCAACCTTGCTCTGGCA-GATGCCTTAGCCACCAGTACCCTGCC CTTCCA-GAGTGTGAATTACCTAATGGGAACATG-GCCATTTGGAACCATCCTTT GCAAGATAGTGATCTCCATAGATTAC-TATAACATGTTCACCAGCATATTCACC CTCTGCAC-CATGAGTGTTGATCGATACATTG-CAGTCTGCCACCCTGTCAAGGC CTTAGATTTCCGTACTCCCCGAAATGC-CAAAATTATCAATGTCTGCAACTGGA TCCTCTCT-TCAGCCATTGGTCTTCCTGTAATGT-TCATAGCTACAACAAAATAC AGGCAAGGTTCCATAGATTGTACACTAA-CATTCTCTCATCCAACCTGGTACTG GGAAAACCT-GCTGAAGATCTGTGTTTTCATCTTCGC-CTTCATTATGCCAGTGC TCATCATTACCGTGTGCTATGGACTGAT-GATCTTGCGCCTCAAGAGTGTCCGC ATGCTCTCTG-GCTCCAAAGAAAAGGACAGGAATCTTC-GAAGGATCACCAGGA TGGTGCTGGTGGTGGTGGCTGTGT-TCATCGTCTGCTGGACTCCCATTCACATT TACGT-CATCATTAAAGCCTTGGTTACAATCCCA-GAAACTACGTTCCAGACTGT TTCTTGGCACTTCTGCATTGCTCTAGGT-TACACAAACAGCTGCCTCAACCCAG TCCTTTATG-CATTTCTGGATGAAAACTTCAAACGAT-GCTTCAGAGAGTTCTGT ATCCCAACCTCTTCCAACATTGAGCAA-CAAAACTCCACTCGAATTCGTCAGA ACACTA-GAGACCACCCCTCCACGGCCAATA-CAGTGGATAGAACTAATCATCA GGTACGCAGTCTCTAGAATTAGG-TATATCTACTGGGGATGACATAAAAATTA TAAG-GCTTTGTGCTAAACTAGGAGTTTAATC-CATTATAGAGGATGAGAATGG AGGGAAGCTT-3' (SEQ ID NO:13).

Example 2

Detecting mu3 Opiate Receptor Expression

Human heart, vein, and artery tissue samples were homogenized in TRI REAGENT (Molecular Research Center, Inc., Cincinnati, Ohio) using a polytron homogenizer. Human white blood cell samples were homogenized in TRI REAGENT by passing the samples through a 1 mL pipette ten times. The homogenates were stored at room temperature for 5 minutes to allow complete dissociation of nucleoprotein. 0.1 mL of 1-bromo-3-chloropropane (BCP) per 1 mL of TRI Reagent was added to the homogenates. The samples were vortexed vigorously for 15 seconds and then stored at room temperature for 7 minutes. After centrifugation of the samples for 15 minutes at 12,000 g, the aqueous phase was transferred to a fresh tube. RNA was precipitated by mixing with 0.5 mL of isopropanol per 1 mL of TRI REAGENT used in for the initial homogenization. Samples were stored at room temperature for 6 minutes and then centrifuged at 12,000 g for 8 minutes at 4° C. After removing the supernatant, the RNA pellet was washed with 1 mL of 75% ethanol per 1 mL TRI REAGENT used for the initial homogenization, and subsequently centrifuged at 7,500 g for 5 minutes at 4° C. The ethanol was discarded, and the RNA pellet air-dried for 5 minutes. The RNA pellet was dissolved in water and used as template.

An aliquot of each RNA sample was separated in an 1% agarose gel stained with ethidium bromide. Two predominant bands of small (~2 kb) and large (~5 kb) ribosomal RNA were observed. In addition, spectrophotometric measurements of the RNA samples were analyzed at 260 and 280 nm. The 260/280 ratios from all of the samples were above 1.6.

PCR analysis was used to study the expression of mRNA encoding a human mu3 opiate receptor. Briefly, PCR analysis was performed using the following primers: 5'-GGTACTGGGAAAACCTGCTGAAGATCTGTG-3' (SEQ ID NO:19) and 5'-CATCCATGACCACAGTGGGCAAG-GCAC-3' (SEQ ID NO:20). Separation of the PCR products by gel electrophoresis revealed a large (about 910 bp) and small (about 605 bp) band for each of the four tissue samples (human heart, vein, and artery tissue and human white blood cells). The intensity of the large band for the human white blood cell sample was greater than the intensity of the large band for the human heart, vein, and artery samples. In addition, the intensity of the small band was about the same for the four samples. This result indicates that the mRNA corresponding to the larger band is expressed at a higher level in white blood cells when compared to its level of expression in vascular tissue.

Each band from each sample was purified, cloned into a TA cloning vector, and sequenced. The smaller band (about 605 bp) had a nucleic acid sequence corresponding to the nucleic acid sequence that encodes a human mu3 opiate receptor (e.g., SEQ ID NO:4). The larger band (about 910 bp) had the following nucleic acid sequence: 5'-TGGT-GCTGGTGGTGGTGGCTGTGTTCATCGTCTGCTGG-ACTCCCATTCACATTTA CGTCATCATTAAAGCCTTG-GTTACAATCCCAGAAACTACGTTCCAGACTGTTT CTTGGCACTTCTGCATTGCTCTAGGTTA-CACAAACAGCTGCCTCAACCCAGTC CTTTATG-CATTTCTGGATGAAAACTTCAAACGAT-GCTTCAGAGAGTTCTGTAT CCCAACCTCTTCCAACATTGAGCAA-CAAAACTCCACTCGAATTCGTCAGAAC ACTA-GAGACCACCCCTCCACGGCCAATA-CAGTGGATAGAACTAATCATCAGG TACGCAGTCTCTAGAATTAGGTATATC-TACTGGGGATGACATAAAAATTATA AGGCTTTGT-GCTAAACTAGGAGTTTAATCCATTATA-GAGGATGAGAATGGAG GAAGGGAAAGCAAATTGTGGTT-TAAGGGTTAAAGAAGAGGTTTGTATATAAA CTGGGGTCCTTTAAATTTGCCTGTA-CATATTCATTAAGGTTTAAGGATCCCCA ATGGGNAAAACCATG-GAACTTTTCAAAATACCTTTTTTATGGC-CTTTACTTTT ATGCAAAATTTATGACTTTAGCACAT-TATAGAAATAATTCTGATCTAGAATCC TTTTCATTTTCCCCAGAATTAT-TATATAATTCATAGATGTTCTGCAATACCCCT CTTATTTCTCAAAAGCCAGTCT- TGCTCTGGTTTCTGGATTAAAGAGAGAGGGT GAGTGCCTTGCCCACTGTGGTCATGGATGCAAGAT- ATTCACAGAAAATTAGC ATCATAGAAAAAAAANN- NAAAAAAAAAAAAAAAAAAANCATGTCGGCCGCCT CGGCCAAACATCGGGTCGAGCATG- CATCTAGGGCGGCCAATTCCGCCCTCT CCCCCCCNGCNNTTT-3' (SEQ ID NO:21). The mRNA corresponding to the 910 bp band was designated a mu4 opiate receptor, while the mRNA corresponding to the 605 bp band was designated a mu3 opiate receptor.

Real time RT-PCR was performed using the same primers and RNA samples. The results confirmed that the mu3 mRNA is expressed equally in human heart, vein, artery, and white blood cells. In addition, the results confirmed that the mu4 mRNA is expressed to a greater extent in human heart, vein, and artery than in human white blood cells.

The following nucleic acid sequence was unique to the mu4 opiate receptor sequence: 5'-GGAAGGGAAAG- CAAATTGTGGTTTAAGGGTTAAAGAA- GAGGTTTGTATATAAACTGGGGTCCTT- TAAATTTGCCTGTACATATTCATTAAGGTTT AAGGATCCCCAATGGGNAAAACCATG- GAACTTTTCAAAATACCTTTTTATG GCCTT- TACTTTTATGCAAAATTTATGACTTTAG- CACATTATAGAAATAATTCT GATCTAGAATCCTTTTCATTTTCCC-3' (SEQ ID NO:22). The following nucleic acid sequence corresponds to the 5' end of SEQ ID NO:4 and the 3' end of SEQ ID NO:21: 5'-ATACACCAAGATGAAGACTGCCACCAA- CATCTACATTTTCAACCTTGCTCTGGCA- GATGCCTTAGCCACCAGTACCCTGCCCT- TCCAGAGTGTGAATT ACCTAATGGGAACATGGCCATTTGGAAC- CATCCTTTGCAAGATAGTGATCTCC ATAGATTAC- TATAACATGTTCACCAGCATATTCAC- CCTCTGCACCATGAGTGT TGATCGATACATTGCAGTCTGCCACCCT- GTCAAGGCCTTAGATTTCCGTACTC CCCGAAATGC- CAAAATTATCAATGTCTGCAACTGGATC- CTCTCTTCAGCCATT GGTCTTCCTGTAATGTTCATAGCTACAA- CAAAATACAGGCAAGGTTCCATAG ATTGTACAC- TAACATTCTCTCATCCAACCTGG- TACTGGGAAAACCTGCTGAAG ATCTGTGTTTTCATCTTCGCCTTCAT- TATGCCAGTGCTCATCATTACCGTGTGC TATGGACT- GATGATCTTGCGCCTCAAGAGTGTCCG- CATGCTCTCTGGCTCCAA AGAAAAGGACAGGAATCTTCGAAGGAT- CACCAGGATGGTGCTGGTGGTGGT GGCTGTGT- TCATCGTCTGCTGGACTCCCATTCA- CATTTACGTCATCATTAAAG CCTTGGTTACAATCCCAGAAACTACGT- TCCAGACTGTTTCTTGGCACTTCTGC ATTGCTCTAGGTTACACAAACAGCTGC- CTCAACCCAGTCCTTTATGCATTTCT GGAT- GAAAACTTCAAACGATGCTTCAGAGAGT- TCTGTATCCCAACCTCTTCCA ACATTGAGCAACAAAACTCCACTCGAAT- TCGTCAGAACACTAGAGACCACCC CTCCACGGC- CAATACAGTGGATAGAACTAATCATCAG- GTACGCAGTCTCTAG AATTAGGTATATCTACTGGGGATGACAT- AAAAATTATAAGGCTTTGTGCTAA ACTAGGAGTT- TAATCCATTATAGAGGATGAGAATG- GAGGGAAGGGAAAGCA AATTGTGGTTTAAGGGTTAAAGAAGAG- GTTTGTATATAAACTGGGGTCCTTTA AATTTGCCTG- TACATATTCATTAAGGTTTAAGGATC- CCCAATGGGNAAAACC ATGGAACTTTTCAAAATACCTTTTT- TATGGCCTTTACTTTTATGCAAAATTTAT GACTT- TAGCACATTATAGAAATAATTCT- GATCTAGAATCCTTTTCATTTTCCCC AGAATTATTATATAATTCATAGATGT- TCTGCAATACCCCTCTTATTTCTCAAA AGCCAGTCT- TGCTCTGGTTTCTGGATTAAA- GAGAGAGGGTGAGTGCCTTGCCC ACTGTGGTCATGGATGCAAGATATTCA- CAGAAAATTAGCATCATAGAAAAAA AANNNAAAAAAAAAAAAAAAAAAANCAT- GTCGGCCGCCTCGGCCAAACATCG GGTCGAGCAT- GCATCTAGGGCGGCCAATTCCGC- CCCTCTCCCCCCCNGCNNTT TCCACACCGAGGAGTCCAGTTTGTGCAA- GACACCCAGCGGAACCAAAACCCA TCGTGGTAT- GTGAATCGAAGTCATCATAAAAGGTGAC- CCTTCTGTCTGTAAGA TTTTAATTTAAGCATATATTTATGACCT- CAACAAAGACGAACCATCTTTTGTT AATTCACCG- TAGTAACACATAAAGTTATGCTACCTCT- GATCAAAG-3' (SEQ ID NO:23).

Example 3

Additional Cloning Techniques

A nucleic acid molecule encoding a mu3 or mu4 polypeptide is cloned using a human testis Creator SMART cDNA library constructed in pDNR-LIB, a Creator donor vector. This vector has a probability of greater than 93 percent of obtaining a full-length cDNA. Once obtained, the full-length cDNA is sequenced and cloned into an expression vector such as pCMV-Sport-bgal (Life Technologies). The expression vector containing the nucleic acid encoding a mu3 or mu4 polypeptide is transfected into mammalian cells (e.g., CHO or Cos7) by, for example, by Lipofection. Once transfected, the mammalian cells are analyzed for morphine and opioid peptide binding as well as naloxone sensitivity.

In addition, mRNA expression of a mu3 or mu4 opiate receptor is analyzed by RT-PCR using real time PCR (Gene-Amp 5700 sequence detection; Applied Biosystems) or by Northern blot analysis using a sequence-specific probe as described herein.

The following procedures are performed to express nucleic acid encoding a polypeptide having opioid receptor activity. Briefly, a mu3 or mu4 cDNA obtained from the library is cloned into a pcDNA5/FRT/TO-TOPO expression vector (pcDNA5/FRT/TO TA Expression Kit, Invitrogen). This 5.2 kb expression vector is designed to facilitate rapid cloning and tetracycline-regulated expression of PCR products using the Flp-In T-REX System. The expression vector containing the gene of interest is cotransfected with the pOG44 Flp recombinase expression plasmid into a Flp-In T-REX mammalian host cell line (Flp-In CHO) by lipid mediated transfection (Invitrogen), and the pcDNA5/FRT/TO-TOPO vector plus the DNA insert is integrated in a Flp recombinase-dependent manner into the genome. Addition of tetracycline to the culture medium causes expression of the polypeptide encoded by the insert. The pcDNA5/FRT/TO-TOPO expression vector is controlled by the strong human CMV immediate early enhancer/promoter into which the tet operator 2 (TetO2) sequence have been inserted in tandem. Insertion of these TetO2 sequences into the CMV promoter confers regulation by tetracycline to the promoter. PCR primers are designed to ensure that the right recombinant protein is obtained. A pcDNA5/FRT/TO/CAT positive control vector and a mock transfection (negative control) is used to evaluate the results. The CAT protein expressed from the positive control plasmid is determined by ELISA or Western blot assays. Human mu3 or mu4 opiate receptor polypeptide expression is determine by Western blot using polyclonal antibodies specific for either the human mu3 or mu4 polypeptides. Polyclonal antibody that recognize these polypeptides are generated commercially. After identifying cells expressing the mu3 or mu4 polypeptide, functions such as the ability of morphine to cause the induction of cNOS is evaluated. In addition, mu antagonists such as naloxone and CTOP are used in addition to the NO synthase inhibitor, L-NAME, to evaluate the activity of the mu3 or mu4 polypeptide.

Example 4

Detecting mu4 mRNA Expression

Human heparinized whole blood cells obtained from volunteer blood donors (Long Island Blood Services; Melville, N.Y.) were immediately separated using the 1-Step Polymorphs (Accurate Chemical and Scientific Corporation, Westbury, N.Y.) gradient medium. Five mL of the heparinized blood was layered over 3.5 mL of polymorphs in a 14 mL round-bottom tube and centrifuged for 35 minutes at 500×g in a swinging-bucket rotor at 18° C. After centrifugation, the top band at the sample/medium interface consisting of mononuclear cells was harvested in 14 mL tubes and then washed with RPMI 1640 media (GIBCO BRL, Gaithesburg, Md.) by centrifugation for 10 minutes at 400× g. In addition, residual red blood cells were lysed using ACK lysing buffer (Current Protocol in Immunology). The mononuculear cells were incubated in RPMI 1640 supplemented with 10% fetal calf serum for 4 hours in a 37° C. incubator with 5% $CO_2$ in order to recover. The cells were then treated with SNAP (1 µM), SNAP plus superoxide dismutase (SOD; 100 units/mL) (SIGMA St. Louis, Mo.), or SOD (100 U/mL), respectively.

After incubation, mononuclear cells were pelleted by centrifugation, and total RNA was isolated with the RNeasy Protect Mini Kit (Qiagen, Stanford, Calif.) following the directions supplied by the manufacturer. RNA was eluted with 50 µL of RNase-free water.

First strand cDNA synthesis was performed using random hexamers (GIBCO, BRL, Gaithesburg, Md.). 3 µg of total RNA isolated from human mononuclear cells were denatured at 95° C. and reverse transcribed at 40° C. for 1 hour using Superscript II Rnase H-RT (GIBCO BRL, Gaithesburg Md.). Five µL of the RT product was used for the real-time PCR reaction.

Primers and probe specific for the mu4 opiate receptor sequence were designed as follows using the software Primer Express (Applied Biosystems). The sequence for the forward primer was 5'-GAATCCTTTTCATTTTCCCCA-GAAT-3' (SEQ ID NO:24); the sequence for the reverse primer was 5'-AACCAGAGCAAGACTGGCTTTTG-3' (SEQ ID NO:25); and the sequence for the Taqman probe was 5'-ATAATTCATAGATGTTGCTGCAATAC-CCCTCTTATTTCT-3' (SEQ ID NO:26). The Taqman probe was constructed with the 5' reporter dye 6-carboxyfluorescein and a 3' quencher dye 6-carboxy-tetramethyl-rhodoamine. The 2× universal master mix (Applied Biosystems) containing PCR buffer, $MgCl_2$, dNTPs, and the thermal stable AmpliTaq Gold DNA polymerase was used in the PCR reactions. In addition, 200 µM of reverse and forward primers, 100 µM Taqman probe, 5 µL of RT product, and Rnase/DNase-free water were added to the master mix to a final volume of 50 µL. The PCR reaction mixture was transferred to a MicroAmp optical 96-well reaction plate and incubated at 95° C. for 10 minutes to activate the Amplitaq Gold DNA polymerase. The reactions were performed with 40 cycles at 95° C. for 30 seconds and 60° C. for 1 minute on the Applied Biosystems GeneAmp 5700 Sequence Detection System. The PCR results were analyzed with the GeneAmp 5700 SDS software (Applied Biosystems). In order to determine the relative copy number of the target gene transcript, control cDNA generated from SHY cell total RNA was used to produce a standard curve. A standard curve for the reference gene β-actin was performed using the Applied Biosystems β-actin TaqMan Control Reagents kit (part no. 401846). Viability counts were done for all of the different time points, and 96% of the mononuclear cells were viable.

Figure 2:
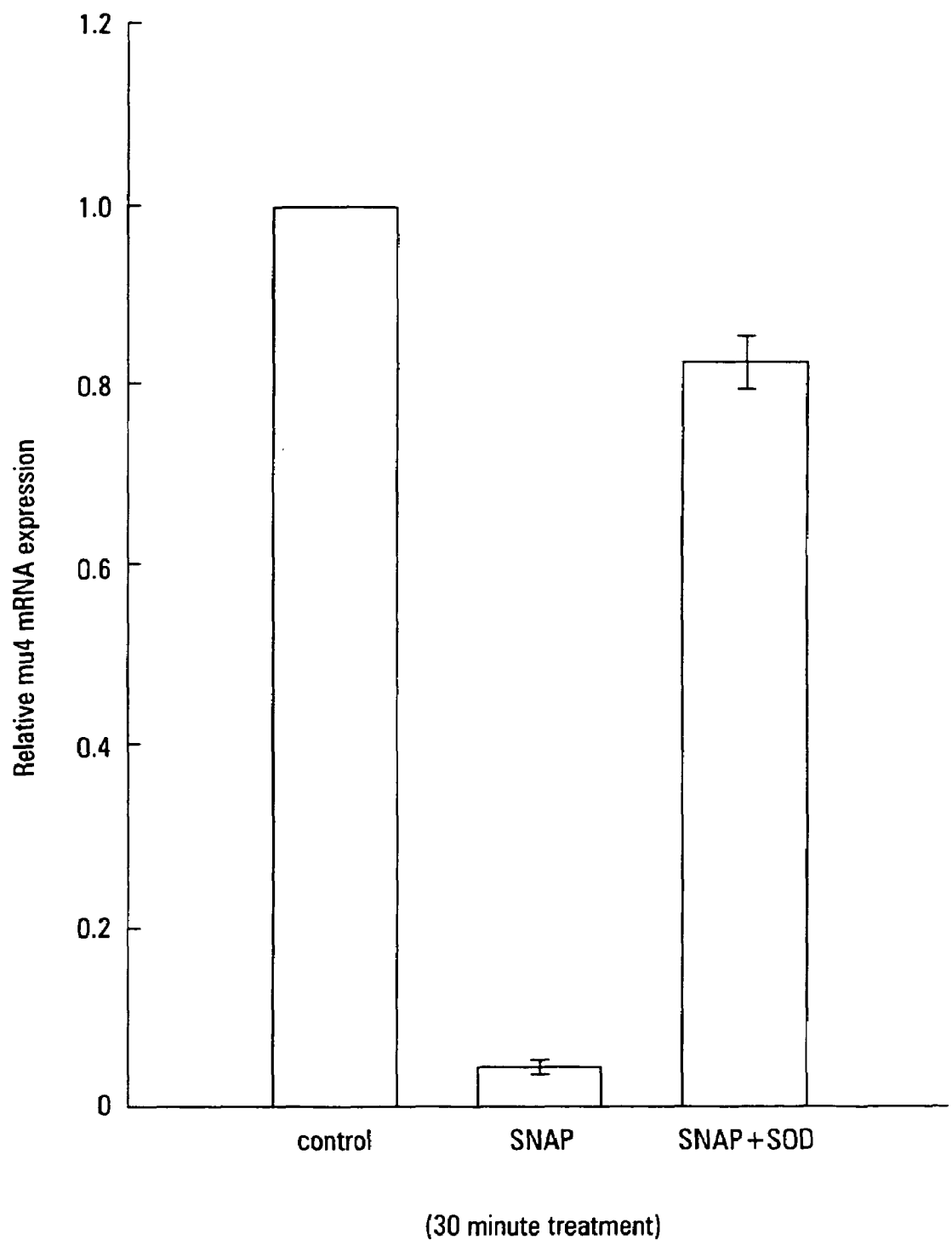
FIG. 2 is a bar graph plotting the relative mu4 mRNA expression level in mononuclear cells for the indicated treatments.
Figure 3:
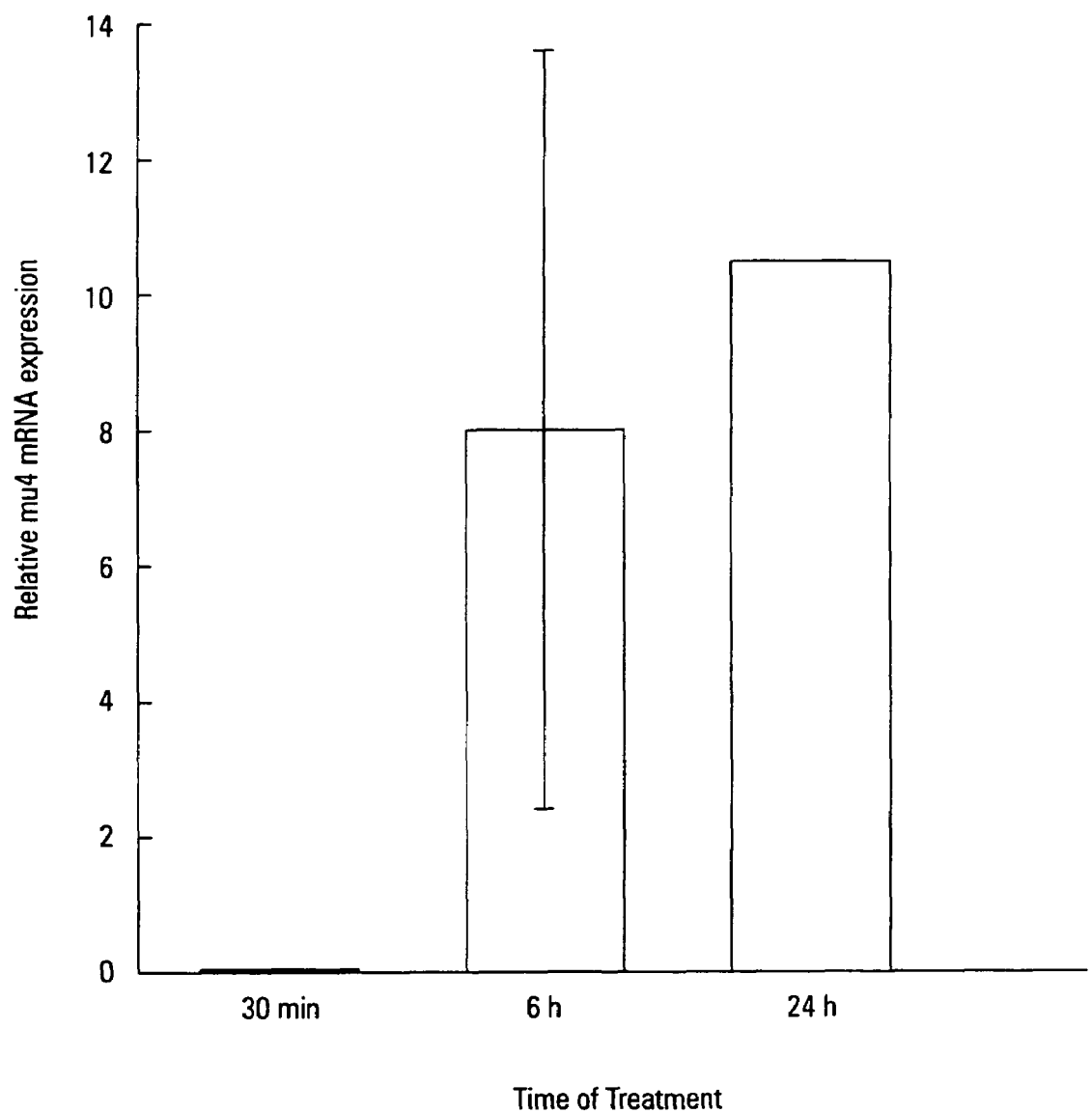
FIG. 3 is a bar graph plotting the relative mu4 mRNA expression level in mononuclear cells treated with SNAP for the indicated durations.
Figure 4:
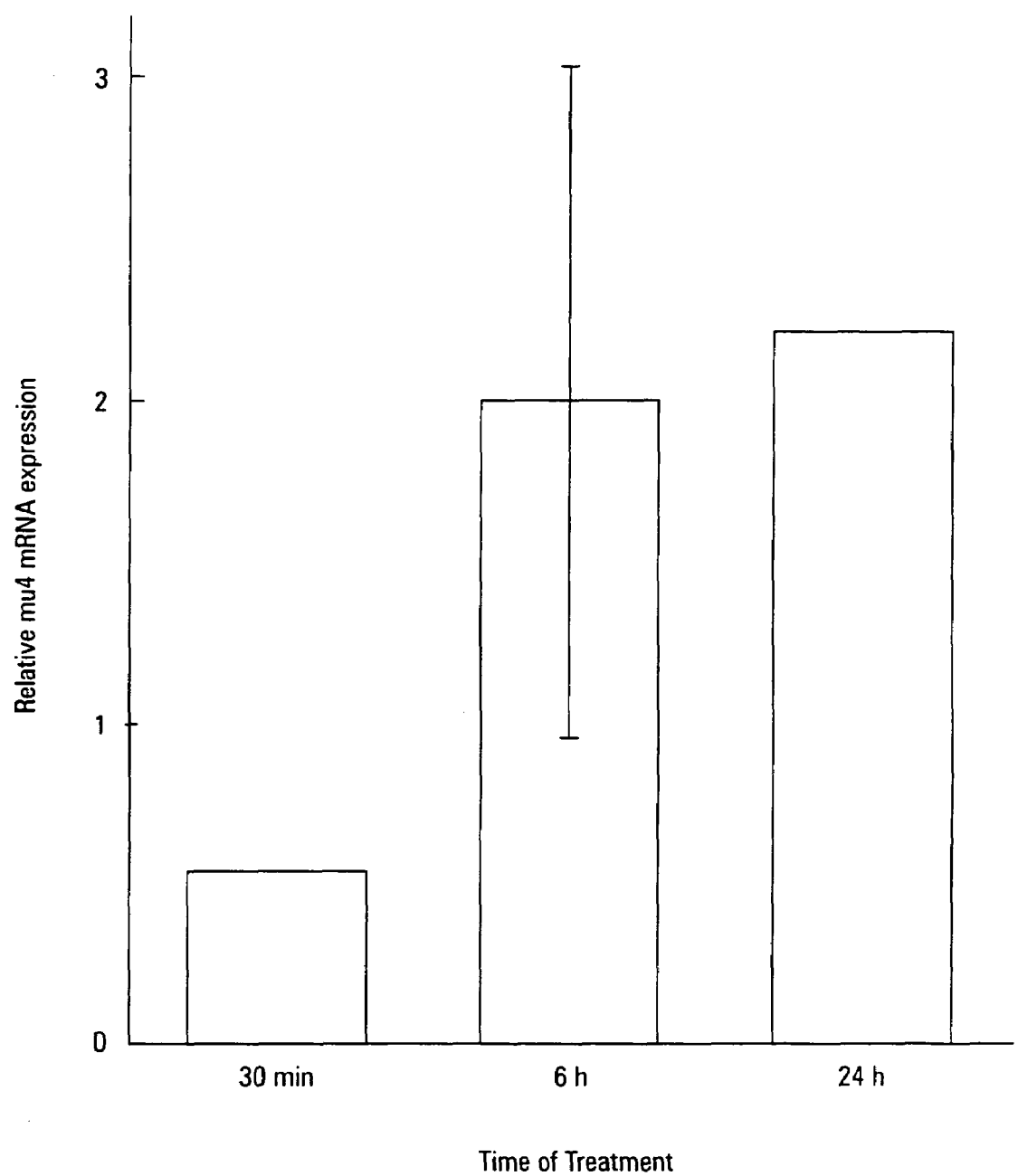
FIG. 4 is a bar graph plotting the relative mu4 mRNA expression level in mononuclear cells treated with morphine for the indicated durations.

Real-time RT-PCR analysis of human mononuclear cells treated with SNAP alone for 30 minutes resulted in significantly lower mu4 mRNA expression (0.05 relative mRNA level) as compared to nontreated cells (1.0 relative mRNA level), whereas cells treated with SNAP plus SOD (which scavenges free radicals) for the same time period exhibited a level of mu4 mRNA expression (0.83 relative mRNA level) close to the observed control level (FIG. 2). After 6 hours of treatment, the level of mu4 mRNA expression in cells treated with SNAP not only rebounded back but also significantly (p=0.029) exceeded control levels (8±5.6 relative mRNA level; FIG. 3). After 24 hours of treatment, the level of mu4 mRNA expression in cells treated with SNAP also exceeded control levels (n=1; 10.5 relative mRNA level; FIG. 3). Similar results were observed in human mononuclear cells treated with morphine (1 µM; FIG. 4).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule that encodes a polypeptide having mu3 opiate receptor activity and comprising the amino acid sequence set forth in SEQ ID NO:2.

2. The isolated nucleic acid molecule of claim 1, wherein said isolated nucleic acid molecule hybridizes under moderately or highly stringent hybridization conditions to the sense or antisense strand of the sequence set forth in SEQ ID NO:1 or 3.

3. The isolated nucleic acid molecule of claim 1, wherein said isolated nucleic acid molecule comprises the sequence set forth in SEQ ID NO:4, 6, 8, or 10.

4. The isolated nucleic acid molecule of claim 1, wherein said isolated nucleic acid molecule hybridizes under moderately stringent hybridization conditions to the sense or antisense strand of the sequence set forth in SEQ ID NO:1.

5. The isolated nucleic acid molecule of claim 1, wherein said isolated nucleic acid molecule hybridizes under highly stringent hybridization conditions to the sense or antisense strand of the sequence set forth in SEQ ID NO:1.

6. The isolated nucleic acid molecule of claim 1, wherein said isolated nucleic acid molecule hybridizes under moderately stringent hybridization conditions to the sense or antisense strand of the sequence set forth in SEQ ID NO:3.

7. The isolated nucleic acid molecule of claim 1, wherein said isolated nucleic acid molecule hybridizes under highly stringent hybridization conditions to the sense or antisense strand of the sequence set forth in SEQ ID NO:3.

8. The isolated nucleic acid molecule of claim 1, wherein said isolated nucleic acid molecule comprises the sequence set forth in SEQ ID NO:1.

9. The isolated nucleic acid molecule of claim 1, wherein said isolated nucleic acid molecule comprises the sequence set forth in SEQ ID NO:3.

10. The isolated nucleic acid molecule of claim 1, wherein said isolated nucleic acid molecule comprises the sequence set forth in SEQ ID NO:4.

11. The isolated nucleic acid molecule of claim 1, wherein said isolated nucleic acid molecule comprises the sequence set forth in SEQ ID NO:6.

12. The isolated nucleic acid molecule of claim 1, wherein said isolated nucleic acid molecule comprises the sequence set forth in SEQ ID NO:8.

13. The isolated nucleic acid molecule of claim 1, wherein said isolated nucleic acid molecule comprises the sequence set forth in SEQ ID NO:10.

* * * * *

UNITED STATES PATENT AND TRADEMARK OFFICE
CERTIFICATE OF CORRECTION

| | |
|---|---|
| PATENT NO. | : 7,285,655 B2 |
| APPLICATION NO. | : 11/454213 |
| DATED | : October 23, 2007 |
| INVENTOR(S) | : Patrick Cadet and George B. Stefano |

It is certified that error appears in the above-identified patent and that said Letters Patent is hereby corrected as shown below:

Column 19, line 10, replace "RLCC" with --RCCC--.

Column 19, line 11, replace "RLCC" with --RCCC--.

Column 20, line 55, replace "RLCC" with --RCCC--.

Column 21, line 55, replace "RLCC" with --RCCC--.

Column 22, line 53, replace "RLCC" with --RCCC--.

Column 23, line 41, replace "HRLC" with --HRCC--.

Column 31, line 20 (after bold line), replace
"Asn Tyr Tyr Ile Ile His Arg Leu Cys Cys Asn Thr Pro Leu Ile Ser" with
--Asn Tyr Tyr Ile Ile His Arg Cys Cys Cys Asn Thr Pro Leu Ile Ser--.

Column 33, line 71 (after bold line), replace
"Asn Tyr Tyr Ile Ile His Arg Leu Cys Cys Asn Thr Pro Leu Ile Ser" with
--Asn Tyr Tyr Ile Ile His Arg Cys Cys Cys Asn Thr Pro Leu Ile Ser--.

Column 37, line 67 (after bold line), replace
"His Gln Asn Tyr Tyr Ile Ile His Arg Leu Cys Cys Asn Thr Pro Leu" with
--His Gln Asn Tyr Tyr Ile Ile His Arg Cys Cys Cys Asn Thr Pro Leu--.

Column 41, line 45 (after bold line), replace
"Thr Asn His Gln Asn Tyr Tyr Ile Ile His Arg Leu Cys Cys Asn Thr" with
--Thr Asn His Gln Asn Tyr Tyr Ile Ile His Arg Cys Cys Cys Asn Thr--.

UNITED STATES PATENT AND TRADEMARK OFFICE
CERTIFICATE OF CORRECTION

PATENT NO.         : 7,285,655 B2
APPLICATION NO.    : 11/454213
DATED              : October 23, 2007
INVENTOR(S)        : Patrick Cadet and George B. Stefano It is certified that error appears in the above-identified patent and that said Letters Patent is hereby corrected as shown below:

Column 45, line 22, (after bold line), replace
"His Gln Asn Tyr Tyr Ile Ile His Arg Leu Cys Cys Asn Thr Pro Leu" with
--His Gln Asn Tyr Tyr Ile Ile His Arg Cys Cys Cys Asn Thr Pro Leu--.

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 29

<210> SEQ ID NO 1
<211> LENGTH: 81

<212> TYPE: DNA
<213> ORGANISM: Homo Sapiens

<400> SEQUENCE: 1

```
aattattata taattcatag atgttgctgc ataccccctc ttatttctca aaagccagtc    60
ttgctctggt tctgtgatta a                                              81
```

<210> SEQ ID NO 2
<211> LENGTH: 26
<212> TYPE: PRT
<213> ORGANISM: Homo Sapiens
<220> FEATURE:
<223> OTHER INFORMATION: Peptide fragment

<400> SEQUENCE: 2

Asn Tyr Tyr Ile Ile His Arg Leu Cys Cys Asn Thr Pro Leu Ile Ser
 1               5                  10                  15

Gln Lys Pro Val Leu Leu Trp Phe Cys Asp
            20                  25

<210> SEQ ID NO 3
<211> LENGTH: 262
<212> TYPE: DNA
<213> ORGANISM: Homo Sapiens
<220> FEATURE:
<221> NAME/KEY: misc_feature
<222> LOCATION: (1)...(262)
<223> OTHER INFORMATION: n = A,T,C or G

<400> SEQUENCE: 3

```
aattattata taattcatag atgttgctgc ataccccctc ttatttctca aaagccagtc    60
ttgctctggt tctgtgatta agagagagg gtgagtgcct tgcccactgt ggtcatggat    120
gcaagatatt cacagaaaat tagcatcata gaaaaaaaan nnaaaaaaaa aaaaaaaaa    180 ncatgtcggc cgcctcggcc aaacatcggg tcgagcatgc atctagggcg gccaattccg    240
cccctctccc ccccngcnnt tt                                            262
```

<210> SEQ ID NO 4
<211> LENGTH: 945
<212> TYPE: DNA
<213> ORGANISM: Homo Sapiens

<400> SEQUENCE: 4

```
atgaagactg ccaccaacat ctacattttc aaccttgctc tggcagatgc cttagccacc    60
agtaccctgc ccttccagag tgtgaattac ctaatgggaa catggccatt tggaaccatc    120
ctttgcaaga tagtgatctc catagattac tataacatgt tcaccagcat attcacccctc    180 tgcaccatga gtgttgatcg atacattgca gtctgccacc ctgtcaaggc cttagatttc    240
cgtactcccc gaaatgccaa aattatcaat gtctgcaact ggatcctctc ttcagccatt    300
ggtcttcctg taatgttcat ggctacaaca aaatacaggc aaggttccat agattgtaca    360
ctaacattct ctcatccaac ctggtactgg gaaaacctgc tgaagatctg tgttttcatc    420
ttcgccttca ttatgccagt gctcatcatt accgtgtgct atggactgat gatcttgcgc    480
ctcaagagtg tccgcatgct ctctggctcc aagaaaaagg acaggaatct tcgaaggatc    540
accaggatgg tgctggtggt ggtggctgtg ttcatcgtct gctggactcc cattcacatt    600
tacgtcatca ttaaagcctt ggttacaatc cagaaactac gttccagac tgtttcttgg    660 cacttctgca ttgctctagg ttacacaaac agctgcctca cccagtcct ttatgcattt    720
```

```
ctggatgaaa acttcaaacg atgcttcaga gagttctgta tcccaacctc ttccaacatt      780
gagcaacaaa actccactcg aattcgtcag aacactagag accaccctc cacggccaat       840 acagtggata gaactaatca tcagaattat tatataattc atagatgttg ctgcaatacc      900
cctcttattt ctcaaaagcc agtcttgctc tggttctgtg attaa                     945
```

<210> SEQ ID NO 5
<211> LENGTH: 314
<212> TYPE: PRT
<213> ORGANISM: Homo Sapiens

<400> SEQUENCE: 5

```
Met Lys Thr Ala Thr Asn Ile Tyr Ile Phe Asn Leu Ala Leu Ala Asp
 1               5                  10                  15

Ala Leu Ala Thr Ser Thr Leu Pro Phe Gln Ser Val Asn Tyr Leu Met
             20                  25                  30

Gly Thr Trp Pro Phe Gly Thr Ile Leu Cys Lys Ile Val Ile Ser Ile
         35                  40                  45

Asp Tyr Tyr Asn Met Phe Thr Ser Ile Phe Thr Leu Cys Thr Met Ser
 50                  55                  60

Val Asp Arg Tyr Ile Ala Val Cys His Pro Val Lys Ala Leu Asp Phe
 65                  70                  75                  80

Arg Thr Pro Arg Asn Ala Lys Ile Ile Asn Val Cys Asn Trp Ile Leu
                 85                  90                  95

Ser Ser Ala Ile Gly Leu Pro Val Met Phe Met Ala Thr Thr Lys Tyr
            100                 105                 110

Arg Gln Gly Ser Ile Asp Cys Thr Leu Thr Phe Ser His Pro Thr Trp
        115                 120                 125

Tyr Trp Glu Asn Leu Leu Lys Ile Cys Val Phe Ile Phe Ala Phe Ile
    130                 135                 140

Met Pro Val Leu Ile Ile Thr Val Cys Tyr Gly Leu Met Ile Leu Arg
145                 150                 155                 160

Leu Lys Ser Val Arg Met Leu Ser Gly Ser Lys Glu Lys Asp Arg Asn
                165                 170                 175

Leu Arg Arg Ile Thr Arg Met Val Leu Val Val Val Ala Val Phe Ile
            180                 185                 190

Val Cys Trp Thr Pro Ile His Ile Tyr Val Ile Ile Lys Ala Leu Val
        195                 200                 205

Thr Ile Pro Glu Thr Thr Phe Gln Thr Val Ser Trp His Phe Cys Ile
    210                 215                 220

Ala Leu Gly Tyr Thr Asn Ser Cys Leu Asn Pro Val Leu Tyr Ala Phe
225                 230                 235                 240

Leu Asp Glu Asn Phe Lys Arg Cys Phe Arg Glu Phe Cys Ile Pro Thr
                245                 250                 255

Ser Ser Asn Ile Glu Gln Gln Asn Ser Thr Arg Ile Arg Gln Asn Thr
            260                 265                 270

Arg Asp His Pro Ser Thr Ala Asn Thr Val Asp Arg Thr Asn His Gln
        275                 280                 285

Asn Tyr Tyr Ile Ile His Arg Leu Cys Cys Asn Thr Pro Leu Ile Ser
    290                 295                 300

Gln Lys Pro Val Leu Leu Trp Phe Cys Asp
305                 310
```

<210> SEQ ID NO 6
<211> LENGTH: 1431

```
<212> TYPE: DNA
<213> ORGANISM: Homo Sapiens

<400> SEQUENCE: 6
atgtcagatg ctcagctcgg tcccctccgc ctgacgctcc tctctgtctc agccaggact      60
ggtttctgta agaaacagca ggagctgtgg cagcggcgaa aggaagcggc tgaggcgctt     120
ggaacccgaa aagtctcggt gctcctggct acctcgcaca gcggtgcccg cccggccgtc     180
agtaccatgg acagcagcgc tgcccccacg aacgccagca attgcactga tgccttggcg     240
tactcaagtt gctccccagc acccagcccc ggttcctggg tcaacttgtc ccacttagat     300
ggcaacctgt ccgacccatg cggtccgaac cgcaccgacc tgggcgggag agacagcctg     360
tgccctccga ccggcagtcc ctccatgatc acggccatca cgatcatggc cctctactcc     420
atcgtgtgcg tggtggggct cttcggaaac ttcctggtca tgtatgtgat tgtcagatac     480
accaagatga agactgccac caacatctac attttcaacc ttgctctggc agatgcctta     540
gccaccagta ccctgccctt ccagagtgtg aattacctaa tgggaacatg gccatttgga     600
accatccttt gcaagatagt gatctccata gattactata acatgttcac cagcatattc     660
accctctgca ccatgagtgt tgatcgatac attgcagtct gccaccctgt caaggcctta     720
gatttccgta ctccccgaaa tgccaaaatt atcaatgtct gcaactggat cctctcttca     780
gccattggtc ttcctgtaat gttcatggct acaacaaaat acaggcaagg ttccatagat     840
tgtacactaa cattctctca tccaacctgg tactgggaaa acctgctgaa gatctgtgtt     900
ttcatcttcg ccttcattat gccagtgctc atcattaccg tgtgctatgg actgatgatc     960
ttgcgcctca agagtgtccg catgctctct ggctccaaag aaaaggacag gaatcttcga    1020
aggatcacca ggatggtgct ggtggtggtg gctgtgttca tcgtctgctg gactcccatt    1080
cacatttacg tcatcattaa agccttggtt acaatcccag aaactacgtt ccagactgtt    1140
tcttggcact ctgcattgc tctaggttac acaaacagct gcctcaaccc agtcctttat    1200
gcatttctgg atgaaaactt caaacgatgc ttcagagagt tctgtatccc aacctcttcc    1260
aacattgagc aacaaaactc cactcgaatt cgtcagaaca ctagagacca ccctccacg    1320
gccaatacag tggatagaac taatcatcag aattattata taattcatag atgttgctgc    1380
aatacccctc ttatttctca aaagccagtc ttgctctggt tctgtgatta a             1431
```

<210> SEQ ID NO 7
<211> LENGTH: 476
<212> TYPE: PRT
<213> ORGANISM: Homo Sapiens

<400> SEQUENCE: 7

Met Ser Asp Ala Gln Leu Gly Pro Leu Arg Leu Thr Leu Leu Ser Val
1               5                   10                  15

Ser Ala Arg Thr Gly Phe Cys Lys Lys Gln Gln Glu Leu Trp Gln Arg
            20                  25                  30

Arg Lys Glu Ala Ala Glu Ala Leu Gly Thr Arg Lys Val Ser Val Leu
        35                  40                  45

Leu Ala Thr Ser His Ser Gly Ala Arg Pro Ala Val Ser Thr Met Asp
    50                  55                  60

Ser Ser Ala Ala Pro Thr Asn Ala Ser Asn Cys Thr Asp Ala Leu Ala
65                  70                  75                  80

Tyr Ser Ser Cys Ser Pro Ala Pro Ser Pro Gly Ser Trp Val Asn Leu
                85                  90                  95

```
Ser His Leu Asp Gly Asn Leu Ser Asp Pro Cys Gly Pro Asn Arg Thr
            100                 105                 110

Asp Leu Gly Gly Arg Asp Ser Leu Cys Pro Pro Thr Gly Ser Pro Ser
            115                 120                 125

Met Ile Thr Ala Ile Thr Ile Met Ala Leu Tyr Ser Ile Val Cys Val
130                 135                 140

Val Gly Leu Phe Gly Asn Phe Leu Val Met Tyr Val Ile Val Arg Tyr
145                 150                 155                 160

Thr Lys Met Lys Thr Ala Thr Asn Ile Tyr Ile Phe Asn Leu Ala Leu
                165                 170                 175

Ala Asp Ala Leu Ala Thr Ser Thr Leu Pro Phe Gln Ser Val Asn Tyr
            180                 185                 190

Leu Met Gly Thr Trp Pro Phe Gly Thr Ile Leu Cys Lys Ile Val Ile
            195                 200                 205

Ser Ile Asp Tyr Tyr Asn Met Phe Thr Ser Ile Phe Thr Leu Cys Thr
210                 215                 220

Met Ser Val Asp Arg Tyr Ile Ala Val Cys His Pro Val Lys Ala Leu
225                 230                 235                 240

Asp Phe Arg Thr Pro Arg Asn Ala Lys Ile Ile Asn Val Cys Asn Trp
                245                 250                 255

Ile Leu Ser Ser Ala Ile Gly Leu Pro Val Met Phe Met Ala Thr Thr
            260                 265                 270

Lys Tyr Arg Gln Gly Ser Ile Asp Cys Thr Leu Thr Phe Ser His Pro
            275                 280                 285

Thr Trp Tyr Trp Glu Asn Leu Leu Lys Ile Cys Val Phe Ile Phe Ala
290                 295                 300

Phe Ile Met Pro Val Leu Ile Ile Thr Val Cys Tyr Gly Leu Met Ile
305                 310                 315                 320

Leu Arg Leu Lys Ser Val Arg Met Leu Ser Gly Ser Lys Glu Lys Asp
                325                 330                 335

Arg Asn Leu Arg Arg Ile Thr Arg Met Val Leu Val Val Val Ala Val
            340                 345                 350

Phe Ile Val Cys Trp Thr Pro Ile His Ile Tyr Val Ile Ile Lys Ala
            355                 360                 365

Leu Val Thr Ile Pro Glu Thr Thr Phe Gln Thr Val Ser Trp His Phe
370                 375                 380

Cys Ile Ala Leu Gly Tyr Thr Asn Ser Cys Leu Asn Pro Val Leu Tyr
385                 390                 395                 400

Ala Phe Leu Asp Glu Asn Phe Lys Arg Cys Phe Arg Glu Phe Cys Ile
                405                 410                 415

Pro Thr Ser Ser Asn Ile Glu Gln Gln Asn Ser Thr Arg Ile Arg Gln
            420                 425                 430

Asn Thr Arg Asp His Pro Ser Thr Ala Asn Thr Val Asp Arg Thr Asn
            435                 440                 445

His Gln Asn Tyr Tyr Ile Ile His Arg Leu Cys Cys Asn Thr Pro Leu
450                 455                 460

Ile Ser Gln Lys Pro Val Leu Leu Trp Phe Cys Asp
465                 470                 475

<210> SEQ ID NO 8
<211> LENGTH: 1245
<212> TYPE: DNA
<213> ORGANISM: Homo Sapiens

<400> SEQUENCE: 8
```

```
atggacagca gcgctgcccc cacgaacgcc agcaattgca ctgatgcctt ggcgtactca    60
agttgctccc cagcacccag ccccggttcc tgggtcaact tgtcccactt agatggcaac   120
ctgtccgacc catgcggtcc gaaccgcacc gacctgggcg ggagagacag cctgtgccct   180
ccgaccggca gtcctccat gatcacggcc atcacgatca tggccctcta ctccatcgtg    240
tgcgtggtgg ggctcttcgg aaacttcctg gtcatgtatg tgattgtcag atacaccaag   300
atgaagactg ccaccaacat ctacattttc aaccttgctc tggcagatgc cttagccacc   360
agtaccctgc ccttccagag tgtgaattac ctaatgggaa catggccatt tggaaccatc   420
ctttgcaaga tagtgatctc catagattac tataacatgt tcaccagcat attcaccctc   480
tgcaccatga gtgttgatcg atacattgca gtctgccacc tgtcaaggc cttagatttc    540 cgtactcccc gaaatgccaa aattatcaat gtctgcaact ggatcctctc ttcagccatt   600
ggtcttcctg taatgttcat ggctacaaca aaatacaggc aaggttccat agattgtaca   660
ctaacattct ctcatccaac ctggtactgg gaaaacctgc tgaagatctg tgttttcatc   720
ttcgccttca ttatgccagt gctcatcatt accgtgtgct atggactgat gatcttgcgc   780
ctcaagagtg tccgcatgct ctctggctcc aaagaaaagg acaggaatct tcgaaggatc   840
accaggatgg tgctggtggt ggtggctgtg ttcatcgtct gctggactcc cattcacatt   900
tacgtcatca ttaaagcctt ggttacaatc ccagaaacta cgttccagac tgtttcttgg   960
cacttctgca ttgctctagg ttacacaaac agctgcctca acccagtcct ttatgcattt  1020
ctggatgaaa acttcaaacg atgcttcaga gagttctgta tcccaacctc ttccaacatt  1080
gagcaacaaa actccactcg aattcgtcag aacactagag accacccctc cacggccaat  1140
acagtggata gaactaatca tcagaattat tatataattc atagatgttg ctgcaatacc  1200
cctcttattt ctcaaaagcc agtcttgctc tggttctgtg attaa                  1245
```

<210> SEQ ID NO 9
<211> LENGTH: 414
<212> TYPE: PRT
<213> ORGANISM: Homo Sapiens

<400> SEQUENCE: 9

```
Met Asp Ser Ser Ala Ala Pro Thr Asn Ala Ser Asn Cys Thr Asp Ala
 1               5                  10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
               100                 105                 110

Ala Leu Ala Asp Ala Leu Ala Thr Ser Thr Leu Pro Phe Gln Ser Val
            115                 120                 125

Asn Tyr Leu Met Gly Thr Trp Pro Phe Gly Thr Ile Leu Cys Lys Ile
        130                 135                 140

Val Ile Ser Ile Asp Tyr Tyr Asn Met Phe Thr Ser Ile Phe Thr Leu
```

-continued

```
                145                 150                 155                 160
Cys Thr Met Ser Val Asp Arg Tyr Ile Ala Val Cys His Pro Val Lys
                    165                 170                 175
Ala Leu Asp Phe Arg Thr Pro Arg Asn Ala Lys Ile Ile Asn Val Cys
                180                 185                 190
Asn Trp Ile Leu Ser Ser Ala Ile Gly Leu Pro Val Met Phe Met Ala
            195                 200                 205
Thr Thr Lys Tyr Arg Gln Gly Ser Ile Asp Cys Thr Leu Thr Phe Ser
        210                 215                 220
His Pro Thr Trp Tyr Trp Glu Asn Leu Leu Lys Ile Cys Val Phe Ile
225                 230                 235                 240
Phe Ala Phe Ile Met Pro Val Leu Ile Thr Val Cys Tyr Gly Leu
                    245                 250                 255
Met Ile Leu Arg Leu Lys Ser Val Arg Met Leu Ser Gly Ser Lys Glu
                260                 265                 270
Lys Asp Arg Asn Leu Arg Arg Ile Thr Arg Met Val Leu Val Val Val
                275                 280                 285
Ala Val Phe Ile Val Cys Trp Thr Pro Ile His Ile Tyr Val Ile Ile
        290                 295                 300
Lys Ala Leu Val Thr Ile Pro Glu Thr Thr Phe Gln Thr Val Ser Trp
305                 310                 315                 320
His Phe Cys Ile Ala Leu Gly Tyr Thr Asn Ser Cys Leu Asn Pro Val
                    325                 330                 335
Leu Tyr Ala Phe Leu Asp Glu Asn Phe Lys Arg Cys Phe Arg Glu Phe
                340                 345                 350
Cys Ile Pro Thr Ser Ser Asn Ile Glu Gln Gln Asn Ser Thr Arg Ile
            355                 360                 365
Arg Gln Asn Thr Arg Asp His Pro Ser Thr Ala Asn Thr Val Asp Arg
        370                 375                 380
Thr Asn His Gln Asn Tyr Tyr Ile Ile His Arg Leu Cys Cys Asn Thr
385                 390                 395                 400
Pro Leu Ile Ser Gln Lys Pro Val Leu Leu Trp Phe Cys Asp
                    405                 410
```

<210> SEQ ID NO 10
<211> LENGTH: 1239
<212> TYPE: DNA
<213> ORGANISM: Rattus norvegicus

<400> SEQUENCE: 10

```
atggacagca gcaccggccc agggaacacc agcgactgct cagacccctt agctcaggca      60
agttgctccc cagcacctgg ctcctgggtc aacttgtccc acttagatgg caacctgtcc     120
gacccatgcg gtccgaaccg caccgacctg gcgggagag acagcctgtg ccctccgacc      180
ggcagtccct ccatgatcac ggccatcacg atcatggccc tctactccat cgtgtgcgtg     240
gtggggctct tcggaaactt cctggtcatg tatgtgattg tcagatacac caagatgaag     300
actgccacca acatctacat tttcaacctt gctctggcag atgccttagc caccagtacc     360
ctgcccttcc agagtgtgaa ttacctaatg ggaacatggc catttggaac catcctttgc     420
aagatagtga tctccataga ttactataac atgttcacca gcatattcac cctctgcacc     480
atgagtgttg atcgatacat tgcagtctgc accctgtca aggccttaga tttccgtact     540
ccccgaaatg ccaaaattat caatgtctgc aactggatcc tctcttcagc cattggtctt     600
cctgtaatgt tcatggctac aacaaaatac aggcaaggtt ccatagattg tacactaaca     660
```

```
ttctctcatc aacctggta ctgggaaaac ctgctgaaga tctgtgtttt catcttcgcc    720
ttcattatgc cagtgctcat cattaccgtg tgctatggac tgatgatctt gcgcctcaag    780
agtgtccgca tgctctctgg ctccaaagaa aaggacagga tcttcgaag gatcaccagg    840 atggtgctgg tggtggtggc tgtgttcatc gtctgctgga ctcccattca catttacgtc    900
atcattaaag ccttggttac aatcccagaa actacgttcc agactgtttc ttggcacttc    960
tgcattgctc taggttacac aaacagctgc ctcaacccag tcctttatgc atttctggat   1020
gaaaacttca acgatgctt cagagagttc tgtatcccaa cctcttccaa cattgagcaa   1080
caaaactcca ctcgaattcg tcagaacact agagaccacc cctccacggc aatacagtg   1140 gatagaacta atcatcagaa ttattatata attcatagat gttgctgcaa taccctctt   1200 atttctcaaa agccagtctt gctctggttc tgtgattaa                          1239
```

<210> SEQ ID NO 11
<211> LENGTH: 412
<212> TYPE: PRT
<213> ORGANISM: Rattus norvegicus

<400> SEQUENCE: 11

```
Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Val Asn Leu
            20                  25                  30

Ser His Leu Asp Gly Asn Leu Ser Asp Pro Cys Gly Pro Asn Arg Thr
        35                  40                  45

Asp Leu Gly Gly Arg Asp Ser Leu Cys Pro Pro Thr Gly Ser Pro Ser
    50                  55                  60

Met Ile Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Ile Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270
```

-continued

Arg Asn Leu Arg Arg Ile Thr Arg Met Val Leu Val Val Ala Val
            275                 280                 285

Phe Ile Val Cys Trp Thr Pro Ile His Ile Tyr Val Ile Lys Ala
    290                 295                 300

Leu Val Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Asn Ile Glu Gln Gln Asn Ser Thr Arg Ile Arg Gln
            355                 360                 365

Asn Thr Arg Asp His Pro Ser Thr Ala Asn Thr Val Asp Arg Thr Asn
    370                 375                 380

His Gln Asn Tyr Tyr Ile Ile His Arg Leu Cys Cys Asn Thr Pro Leu
385                 390                 395                 400

Ile Ser Gln Lys Pro Val Leu Leu Trp Phe Cys Asp
                405                 410

<210> SEQ ID NO 12
<211> LENGTH: 2149
<212> TYPE: DNA
<213> ORGANISM: Homo Sapiens

<400> SEQUENCE: 12 gaggggcta tacgcagagg agaatgtcag atgctcagct cggtcccctc cgcctgacgc     60
tcctctctgt ctcagccagg actggtttct gtaagaaaca gcaggagctg tggcagcggc    120
gaaaggaagc ggctgaggcg cttggaaccc gaaaagtctc ggtgctcctg gctacctcgc    180
acagcggtgc ccgcccggcc gtcagtacca tggacagcag cgctgccccc acgaacgcca    240
gcaattgcac tgatgccttg cgtactcaa gttgctcccc agcacccagc cccggttcct    300
gggtcaactt gtcccactta gatggcaacc tgtccgaccc atgcggtccg aaccgcaccg    360
acctgggcgg gagagacagc ctgtgccctc cgaccggcag tccctccatg atcacggcca    420
tcacgatcat ggccctctac tccatcgtgt gcgtggtggg gctcttcgga aacttcctgg    480
tcatgtatgt gattgtcaga taccaccaaga tgaagactgc caccaacatc tacatttca    540 accttgctct ggcagatgcc ttagccacca gtacccctgcc cttccagagt gtgaattacc    600
taatgggaac atggccattt ggaaccatcc tttgcaagat agtgatctcc atagattact    660
ataacatgtt caccagcata ttcacccctct gcaccatgag tgttgatcga tacattgcag    720
tctgccaccc tgtcaaggcc ttagatttcc gtactccccg aaatgccaaa attatcaatg    780
tctgcaactg gatcctctct tcagccattg gtcttcctgt aatgttcatg ctacaacaa    840 aatacaggca aggttccata gattgtacac taacattctc tcatccaacc tggtactggg    900
aaaacctgct gaagatctgt gttttcatct tcgccttcat tatgccagtg ctcatcatta    960
ccgtgtgcta tggactgatg atcttgcgcc tcaagagtgt ccgcatgctc tctggctcca   1020
aagaaaagga caggaatctt cgaaggatca ccaggatggt gctggtggtg gtggctgtgt   1080
tcatcgtctg ctggactccc attcacattt acgtcatcat taaagccttg gttacaatcc   1140
cagaaactac gttccagact gtttcttggc acttctgcat tgctctaggt tacacaaaca   1200
gctgcctcaa cccagtcctt tatgcatttc tggatgaaaa cttcaaacga tgcttcagag   1260
agttctgtat cccaacctct tccaacattg agcaacaaaa ctccactcga attcgtcaga   1320

-continued

```
acactagaga ccacccctcc acggccaata cagtggatag aactaatcat cagctagaaa    1380
atctggaagc agaaactgct ccgttgccct aacagggtct catgccattc cgaccttcac    1440
caagcttaga agccaccatg tatgtggaag caggttgctt caagaatgtg taggaggctc    1500
taattctcta ggaaagtgcc tgcttttagg tcatccaacc tctttcctct ctggccactc    1560
tgctctgcac attagaggga cagccaaaag taagtggagc atttggaagg aaaggaatat    1620
accacaccga ggagtccagt ttgtgcaaga cacccagtgg aaccaaaacc catcgtggta    1680
tgtgaattga agtcatcata aaaggtgacc cttctgtctg taagatttta ttttcaagca    1740
aatatttatg acctcaacaa agaagaacca tcttttgtta agttcaccgt agtaacacat    1800
aaagtaaatg ctacctctga tcaaagcacc ttgaatggaa ggtccgagtc tttttagtgt    1860
tttgcaaggg aatgaatcca ttattctatt ttagactttt aacttcacct taaaattagc    1920
atctggctaa ggcatcattt tcacctccat ttcttggttt tgtattgttt aaaaaaataa    1980
catctctttc atctagctcc ataattgcaa gggaagagat tagcatgaaa ggtaatctga    2040
aacacagtca tgtgtcagct gtagaaaggt tgattctcat gcactgcaaa tacttccaaa    2100
gagtcatcat gggggatttt tcattcttag gctttcagtg gtttgttcc               2149
```

<210> SEQ ID NO 13
<211> LENGTH: 1473
<212> TYPE: DNA
<213> ORGANISM: Homo Sapiens

<400> SEQUENCE: 13

```
gcagaggaga atgtcagatg ctcagctcgg tccctccgc ctgacgctcc tctctgtctc      60
agccaggact ggtttctgta agaaacagca ggagctgtgg cagcggcgaa aggaagcggc    120
tgaggcgctt ggaacccgaa aagtctcggt gctcctggct acctcgcaca gcggtgcccg    180
cccggccgtc agtaccatgg acagcagcgc tgccccacg aacgccagca attgcactga    240
tgccttggcg tactcaagtt gctccccagc acccagcccc ggttcctggg tcaacttgtc    300
ccacttagat ggcgacctgt ccgacccatg cggtccgaac cgcaccgacc tgggcgggag    360
agacagcctg tgccctccaa ccggcagtcc ctccatgatc acggccatca cgatcatggc    420
cctctactcc atcgtgtgcg tggtggggct cttcggaaac ttcctggtca tgtatgtgat    480
tgtcagatac accaagatga agactgccac caacatctac attttcaacc ttgctctggc    540
agatgcctta gccaccagta ccctgccctt ccagagtgtg aattacctaa tgggaacatg    600
gccatttgga accatccttt gcaagatagt gatctccata gattactata acatgttcac    660
cagcatattc acctctgca ccatgagtgt tgatcgatac attgcagtct gccaccctgt    720
caaggcctta gatttccgta ctccccgaaa tgccaaaatt atcaatgtct gcaactggat    780
cctctcttca gccattggtc ttcctgtaat gttcatagct acaacaaaat acaggcaagg    840
ttccatagat tgtacactaa cattctctca tccaacctgg tactgggaaa acctgctgaa    900
gatctgtgtt ttcatcttcg ccttcattat gccagtgctc atcattaccg tgtgctatgg    960
actgatgatc ttgcgcctca gagtgtccg catgctctct ggctccaaag aaaaggacag   1020
gaatcttcga aggatcacca ggatggtgct ggtggtggtg gctgtgttca tcgtctgctg   1080
gactcccatt cacatttacg tcatcattaa agccttggtt acaatcccag aaactacgtt   1140
ccagactgtt tcttggcact ctgcattgc tctaggttac acaaacagct gcctcaaccc   1200
agtcctttat gcatttctgg atgaaaactt caaacgatgc ttcagagagt tctgtatccc   1260
```

```
aacctcttcc aacattgagc aacaaaactc cactcgaatt cgtcagaaca ctagagacca    1320
cccctccacg gccaatacag tggatagaac taatcatcag gtacgcagtc tctagaatta    1380
ggtatatcta ctggggatga cataaaaatt ataaggcttt gtgctaaact aggagtttaa    1440
tccattatag aggatgagaa tggagggaag ctt                                 1473
```

<210> SEQ ID NO 14
<211> LENGTH: 28
<212> TYPE: DNA
<213> ORGANISM: Homo Sapiens
<220> FEATURE:
<223> OTHER INFORMATION: Primer

<400> SEQUENCE: 14

```
ggtactggga aaacctgctg aagatctg                                       28
```

<210> SEQ ID NO 15
<211> LENGTH: 28
<212> TYPE: DNA
<213> ORGANISM: Homo Sapiens
<220> FEATURE:
<223> OTHER INFORMATION: Primer

<400> SEQUENCE: 15

```
ggtctctagt gttctgacga attcgagt                                       28
```

<210> SEQ ID NO 16
<211> LENGTH: 12
<212> TYPE: PRT
<213> ORGANISM: Homo Sapiens
<220> FEATURE:
<223> OTHER INFORMATION: Peptide fragment

<400> SEQUENCE: 16

```
Leu Glu Asn Leu Glu Ala Glu Thr Ala Pro Leu Pro
 1               5                  10
```

<210> SEQ ID NO 17
<211> LENGTH: 13
<212> TYPE: DNA
<213> ORGANISM: Homo Sapiens

<400> SEQUENCE: 17

```
atacaccaag atg                                                       13
```

<210> SEQ ID NO 18
<211> LENGTH: 453
<212> TYPE: DNA
<213> ORGANISM: Homo Sapiens

<400> SEQUENCE: 18

```
ctagaaaatc tggaagcaga aactgctccg ttgccctaac agggtctcat gccattccga    60
ccttcaccaa gcttagaagc caccatgtat gtggaagcag gttgcttcaa gaatgtgtag    120
gaggctctaa ttctctagga aagtgcctgc ttttaggtca tccaacctct ttcctctctg    180
gccactctgc tctgcacatt agagggacag ccaaaagtaa gtggagcatt tggaaggaaa    240
ggaatatacc acaccgagga gtccagtttg tgcaagacac ccagtggaac caaaacccat    300
cgtggtatgt gaattgaagt catcatcaaa ggtgacccct ctgtctgtaa gatttttattt    360 tcaagcaaat atttatgacc tcaacaaaga agaaccatct tttgttaagt tcaccgtagt    420
aacacataaa gtaaatgcta cctctgatca aag                                 453
```

<210> SEQ ID NO 19
<211> LENGTH: 30
<212> TYPE: DNA
<213> ORGANISM: Homo Sapiens
<220> FEATURE:
<223> OTHER INFORMATION: Primer

<400> SEQUENCE: 19
ggtactggga aaacctgctg aagatctgtg                                           30

<210> SEQ ID NO 20
<211> LENGTH: 27
<212> TYPE: DNA
<213> ORGANISM: Homo Sapiens
<220> FEATURE:
<223> OTHER INFORMATION: Primer

<400> SEQUENCE: 20
catccatgac cacagtgggc aaggcac                                              27

<210> SEQ ID NO 21
<211> LENGTH: 910
<212> TYPE: DNA
<213> ORGANISM: Homo Sapiens
<220> FEATURE:
<221> NAME/KEY: misc_feature
<222> LOCATION: (1)...(910)
<223> OTHER INFORMATION: n = A,T,C or G

<400> SEQUENCE: 21
tggtgctggt ggtggtggct gtgttcatcg tctgctggac tcccattcac atttacgtca    60
tcattaaagc cttggttaca atcccagaaa ctacgttcca gactgtttct tggcacttct   120
gcattgctct aggttacaca aacagctgcc tcaacccagt cctttatgca tttctggatg   180
aaaacttcaa acgatgcttc agagagttct gtatcccaac ctcttccaac attgagcaac   240
aaaactccac tcgaattcgt cagaacacta gagaccaccc ctccacggcc aatacagtgg   300
atagaactaa tcatcaggta cgcagtctct agaattaggt atatctactg gggatgacat   360
aaaaattata aggctttgtg ctaaactagg agtttaatcc attatagagg atgagaatgg   420
aggaagggaa agcaaattgt ggtttaaggg ttaaagaaga ggtttgtata taaactgggg   480
tcctttaaat ttgcctgtac atattcatta aggtttaagg atccccaatg ggnaaaacca   540
tggaactttt caaaatacct tttttatggc ctttacttt atgcaaaatt tatgacttta   600
gcacattata gaaataattc tgatctagaa tccttttcat tttccccaga attattatat   660
aattcataga tgttctgcaa tacccctctt atttctcaaa agccagtctt gctctggttt   720
ctggattaaa gagagagggt gagtgccttg cccactgtgg tcatggatgc aagatattca   780
cagaaaatta gcatcataga aaaaaaannn aaaaaaaaaa aaaaaaaanc atgtcggccg   840
cctcggccaa acatcgggtc gagcatgcat ctagggcggc caattccgcc cctctccccc   900 ccngcnnttt                                                            910

<210> SEQ ID NO 22
<211> LENGTH: 225
<212> TYPE: DNA
<213> ORGANISM: Homo Sapiens
<220> FEATURE:
<221> NAME/KEY: misc_feature
<222> LOCATION: (1)...(225)
<223> OTHER INFORMATION: n = A,T,C or G

<400> SEQUENCE: 22

-continued

```
ggaagggaaa gcaaattgtg gtttaagggt taaagaagag gtttgtatat aaactggggt    60
cctttaaatt tgcctgtaca tattcattaa ggtttaagga tccccaatgg gnaaaaccat   120 ggaactttc aaaatacctt ttttatggcc tttacttta tgcaaaattt atgactttag    180
cacattatag aaataattct gatctagaat cctttcatt ttccc                   225
```

<210> SEQ ID NO 23
<211> LENGTH: 1670
<212> TYPE: DNA
<213> ORGANISM: Homo Sapiens
<220> FEATURE:
<221> NAME/KEY: misc_feature
<222> LOCATION: (1)...(1670)
<223> OTHER INFORMATION: n = A,T,C or G

<400> SEQUENCE: 23

```
atacaccaag atgaagactg ccaccaacat ctacattttc aaccttgctc tggcagatgc    60
cttagccacc agtaccctgc ccttccagag tgtgaattac ctaatgggaa catgccatt   120 tggaaccatc ctttgcaaga tagtgatctc catagattac tataacatgt tcaccagcat   180
attcaccctc tgcaccatga gtgttgatcg atacattgca gtctgccacc ctgtcaaggc   240
cttagatttc cgtactcccc gaaatgccaa aattatcaat gtctgcaact ggatcctctc   300
ttcagccatt ggtcttcctg taatgttcat agctacaaca aaatacaggc aaggttccat   360
agattgtaca ctaacattct ctcatccaac ctggtactgg gaaaacctgc tgaagatctg   420
tgttttcatc ttcgccttca ttatgccagt gctcatcatt accgtgtgct atggactgat   480
gatcttgcgc ctcaagagtg tccgcatgct ctctggctcc aaagaaaagg acaggaatct   540
tcgaaggatc accaggatgg tgctggtggt ggtggctgtg ttcatcgtct gctggactcc   600
cattcacatt tacgtcatca ttaaagcctt ggttacaatc ccagaaacta cgttccagac   660
tgtttcttgg cacttctgca ttgctctagg ttacacaaac agctgcctca cccagtcct   720 ttatgcattt ctggatgaaa acttcaaacg atgcttcaga gagttctgta tcccaacctc   780
ttccaacatt gagcaacaaa actccactcg aattcgtcag aacactagag accacccctc   840
cacggccaat acagtggata gaactaatca tcaggtacgc agtctctaga attaggtata   900
tctactgggg atgacataaa aattataagg ctttgtgcta aactaggagt ttaatccatt   960
atagaggatg agaatggagg gaagggaaag caaattgtgg tttaagggtt aaagaagagg   1020
tttgtatata aactggggtc ctttaaattt gcctgtacat attcattaag gtttaaggat   1080
ccccaatggg naaaaccatg gaacttttca aaataccttt tttatggcct ttactttat   1140 gcaaaattta tgactttagc acattataga aataattctg atctagaatc cttttcattt   1200
tccccagaat tattatataa ttcatagatg ttctgcaata cccctcttat ttctcaaaag   1260
ccagtcttgc tctggttct ggattaaaga gagggtga gtgccttgcc cactgtggtc    1320
atggatgcaa gatattcaca gaaaattagc atcatagaaa aaaaannnaa aaaaaaaaa   1380 aaaaaancat gtcggccgcc tcggccaaac atcgggtcga gcatgcatct agggcggcca   1440
attccgcccc tctccccccc ngcnntttcc acaccgagga gtccagtttg tgcaagacac   1500
ccagcggaac caaacccat cgtggtatgt gaatcgaagt catcataaaa ggtgacccct   1560
ctgtctgtaa gattttaatt taagcatata tttatgacct caacaaagac gaaccatctt   1620
ttgttaattc accgtagtaa cacataaagt tatgctacct ctgatcaaag              1670
```

<210> SEQ ID NO 24

```
<211> LENGTH: 25
<212> TYPE: DNA
<213> ORGANISM: Homo Sapiens
<220> FEATURE:
<223> OTHER INFORMATION: Primer

<400> SEQUENCE: 24
gaatcctttt cattttcccc agaat                                              25

<210> SEQ ID NO 25
<211> LENGTH: 23
<212> TYPE: DNA
<213> ORGANISM: Homo Sapiens
<220> FEATURE:
<223> OTHER INFORMATION: Primer

<400> SEQUENCE: 25
aaccagagca agactggctt ttg                                                23

<210> SEQ ID NO 26
<211> LENGTH: 39
<212> TYPE: DNA
<213> ORGANISM: Homo Sapiens
<220> FEATURE:
<223> OTHER INFORMATION: Primer

<400> SEQUENCE: 26
ataattcata gatgttgctg caatacccct cttatttct                               39

<210> SEQ ID NO 27
<211> LENGTH: 20
<212> TYPE: DNA
<213> ORGANISM: Artificial Sequence
<220> FEATURE:
<223> OTHER INFORMATION: Artificial

<400> SEQUENCE: 27
aggtcgtgta ctgtcagtca                                                    20

<210> SEQ ID NO 28
<211> LENGTH: 20
<212> TYPE: DNA
<213> ORGANISM: Artificial Sequence
<220> FEATURE:
<223> OTHER INFORMATION: Artificial

<400> SEQUENCE: 28
acgtggtgaa ctgccagtga                                                    20

<210> SEQ ID NO 29
<211> LENGTH: 5
<212> TYPE: PRT
<213> ORGANISM: Artificial Sequence
<220> FEATURE:
<223> OTHER INFORMATION: Opioid polypeptide
<220> FEATURE:
<221> NAME/KEY: VARIANT
<222> LOCATION: 2
<223> OTHER INFORMATION: Xaa = D-Alanine
<220> FEATURE:
<221> NAME/KEY: VARIANT
<222> LOCATION: 4
<223> OTHER INFORMATION: Xaa = N-methylphenylanine
<220> FEATURE:
<221> NAME/KEY: VARIANT
<222> LOCATION: 5
<223> OTHER INFORMATION: Xaa = Gly(ol)

<400> SEQUENCE: 29
```

```
-continued

Tyr Xaa Gly Xaa Xaa
 1               5
```